US010501743B2

(12) United States Patent
Bachelet et al.

(10) Patent No.: US 10,501,743 B2
(45) Date of Patent: Dec. 10, 2019

(54) METHODS AND COMPOSITIONS FOR SELECTION OF FUNCTIONAL OLIGONUCLEOTIDES

(71) Applicant: Augmanity Nano LTD, Rehovot (IL)

(72) Inventors: Ido Bachelet, Tel Aviv (IL); Noam Mamet, Tel Aviv (IL); Itai Rusinek, Tel Aviv (IL); Gil Harari, Tel Aviv (IL); Anastasia Shapiro, Rishon LeZion (IL); Yaniv Amir, Tel Aviv (IL); Erez Lavi, Tel Aviv (IL); Almogit Abu-Horowitz, Herzliya (IL)

( * ) Notice: Subject to any disclaimer, the term of this patent is extended or adjusted under 35 U.S.C. 154(b) by 0 days.

(21) Appl. No.: 16/165,267

(22) Filed: Oct. 19, 2018

(65) Prior Publication Data

US 2019/0040391 A1   Feb. 7, 2019

Related U.S. Application Data

(63) Continuation of application No. PCT/IB2018/000418, filed on Mar. 30, 2018.

(60) Provisional application No. 62/478,993, filed on Mar. 30, 2017.

(51) Int. Cl.
| | |
|---|---|
| *C12N 15/115* | (2010.01) |
| *B01L 3/00* | (2006.01) |
| *C12N 15/10* | (2006.01) |
| *C12Q 1/6811* | (2018.01) |

(52) U.S. Cl.
CPC ......... *C12N 15/115* (2013.01); *B01L 3/5027* (2013.01); *C12N 15/1048* (2013.01); *C12Q 1/6811* (2013.01); *C12N 2310/16* (2013.01)

(58) Field of Classification Search
CPC . B01L 3/5027; C12N 15/115; C12N 15/1048; C12N 2310/16; C12N 2320/113; C12Q 1/6881
USPC .......... 435/6.1, 6.11, 6.13, 91.1, 91.31, 455; 514/44; 536/23.1, 24.5
See application file for complete search history.

(56) References Cited

FOREIGN PATENT DOCUMENTS

| WO | WO-2000/70329 A1 | 11/2000 | |
|---|---|---|---|
| WO | WO-03/070984 A1 | 8/2003 | |
| WO | WO-2005/037053 A2 | 4/2005 | |
| WO | WO-2005037053 A2 * | 4/2005 | ........... C12N 15/111 |
| WO | WO-2009/140326 A2 | 11/2009 | |
| WO | WO-2009/151688 A2 | 12/2009 | |
| WO | WO-2010/023327 A2 | 3/2010 | |
| WO | WO-2011/050000 A2 | 4/2011 | |
| WO | WO-2014/088830 A2 | 6/2014 | |
| WO | WO-2014088830 A2 * | 6/2014 | ........... C12N 15/1048 |
| WO | WO-2015/077441 A2 | 5/2015 | |
| WO | WO-2015/088455 A1 | 6/2015 | |
| WO | WO-2016/025804 A1 | 2/2016 | |
| WO | WO-2016025804 A1 * | 2/2016 | ........... G01N 33/5308 |
| WO | WO-2018/178770 A2 | 10/2018 | |

OTHER PUBLICATIONS

Sheng et al (ACS Nano, vol. 7, No. 8, pp. 7067-7076. (Year: 2013).*
Kolovskaya et al (Biochemistry Moscow, Suppl. Series A: Membrane and Cell Biology, vol. 8, No. 1, pp. 60-72. (Year: 2014).*
Buenrostro et al., "Quantitative Analysis of RNA-Protein Interactions on a Massively Parallel Array Reveals Biophysical and Evolutionary Landscapes," Nature Biotechnology. 32(6):562-568 (2014).
Collett et al., "Functional RNA Microarrays for High-Throughput Screening of Antiprotein Aptamers," Analytical Biochemistry, 338(1):113-123 (2004).
Hoffmann et al., "Imobilized DNA Aptamers Used as Potent Attractors for Porcine Endothelial Precursor Cells," Journal of Biomedical Materials Research, 84A(3):614-621 (2007).
Kolovskaya et al., "DNA-Aptamer/Protein Interaction as a Cause of Apoptosis and Arrest of Proliferation in Ehrlich Ascites Adenocarcinoma Cells," Biochemistry Supplement Series A: Membrane and Cell Biology, 8(1):60-72 (2014).
McCauley et al., "Aptamer-Based Biosensor Arrays for Detection and Quantification of Biological Macromolecules," Anal Biochem, 319(2):244-250 (2003).
Minseon et al., "Array-based Discovery of Aptamer Pairs," Analytical Chemistry, 87(1):821-828 (2014).
Partial Search Report for International Application No. PCT/IB2018/000418 dated Sep. 14, 2018.
Sheng et al., "Multivalent DNA Nanospheres for Enhanced Capture of Cancer Cells in Microfluidic Devices," ACS Nano, 7(8):7067-7076 (2013).
Tome et al., "Comprehensive Analysis of RNA-Protein Interactions by High-Throughput Sequencing-RNA Affinity Profiling," Nature Methods, 11(6):683-688 (2014).

(Continued)

*Primary Examiner* — Jane J Zara
(74) *Attorney, Agent, or Firm* — Foley Hoag LLP

(57) ABSTRACT

The present disclosure describes compositions and methods for rapid selection of both binding and functional oligonucleotides (DNA, RNA, or any natural or synthetic analog of these). In certain embodiments, provided herein are flow cells (e.g., flow cells for an Illumina sequencing instrument or a Polonator sequencing instrument) comprising within its flow chamber a plurality of immobilized aptamer clusters (e.g., from an aptamer library described herein) and, optionally, one or more target cells (e.g., cancer cells, immune cells, etc.) and/or a detectable indicator of cellular function (e.g., a fluorescent indicator of apoptosis, cell proliferation, gene or protein expression, etc.). In certain embodiments, provided herein are methods of using such an aptamer cluster-containing flow cell to identify functional aptamers from an aptamer library (e.g., in a sequencing instrument, such as an Illumina sequencing instrument).

30 Claims, 5 Drawing Sheets

Specification includes a Sequence Listing.

(56) References Cited

OTHER PUBLICATIONS

Yuan et al., "Fabrication and Characterization of RNA Aptamer Microarrays for the Study of Protein-Aptamer Interacctions with SPR Imagin," Nucleic Acids Research, 34(22):6416-6424 (2006).
International Search Report and Written Opinion for International Application No. PCT/IB2018/000418 dated Dec. 7, 2018.
Kirby et al., "Aptamer-based sensor arrays for the detection and quantitation of proteins," Analytical Chemistry, 76(14):4066-4075 (2004).
Okochi et al., "High-throughput screening of cell death inducible short peptides from TNF?related apoptosis?inducing ligand sequence," FEBS letters, 580(3):885-889 (2006).
Chen et al., "SELMAP—SELEX affinity landscape MAPping of transcription factor binding sites using integrated microfluidics," Sci Reps 6(33351):1-13 (2016).
Franssen-van Hal et al., "Optimized Light-Directed Synthesis of Aptamer Microarrays," Anal Chem 85:5950-5957 (2013).
Gopinath, "Methods developed for SELEX," Anal Bioanal Chem 387:171-182 (2007).
Guo et al., "Cell-SELEX: Novel Perspectives of Aptamer-Based Therapeutics," Int. J. Mol. Sci., 9:668-678 (2008).
Metzker, "Sequencing technologies—the next generation," Nat Revs 11:31-46 (2009).
Mitra et al., "In situ localized amplification and contact replication of many individuals DNA molecules," Nuc Acids Res 27(24):i16/165267-vi (1999).
Pettersson et al., "Generations of sequencing technologies," Gen 93:105-111 (2009).
Sack et al., "Express photolithographic DNA microarray synthesis with optimized chemistry and high-efficiency photolabile groups," J Nanobiotechnol 14:14 (2016).
Seitz et al., "A new method to prevent carry-over contaminations in two-step PCR NGS library preparations," Nuc Acids Res 43(20):1-9 (2015).
Stoltenburg et al., "Capture-SELEX: Selection of DNA Aptamers for Aminoglycoside Antibiotics," J Anal Methods Chem 2012:1-14 (2012).
Stoltenburg et al., "SELEX-A (r)evolutionary method to generate high-affinity nucleic acid ligands," Biomol Eng 24:381-403 (2007).

* cited by examiner

```
                          SEQUENCE LISTING

<160> NUMBER OF SEQ ID NOS: 7

<210> SEQ ID NO 1
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1
gtcacatctc gtatgccgtc ttctgcttga tccagagtga cgcagca            47

<210> SEQ ID NO 2
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 2
ctctttccct acacgacgct cttccgatct actaagccac cgtgtcca           48

<210> SEQ ID NO 3
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 3
gatcggaaga gcacacgtct gaactccagt cacatctcgt atgccg             46

<210> SEQ ID NO 4
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 4
aatgatacgg cgaccaccga gatctacaca cactctttcc ctacacgacg         50
```

```
<210> SEQ ID NO 5
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
tagtatccta ggactctcga gtcaatgcgc aacgtcgcac gag                43

<210> SEQ ID NO 6
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 6
tagtatccta tccaaggatt accaggagcc ccgttccctg acg                43

<210> SEQ ID NO 7
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
tagtatccta ctcactcgta tggtcctacg gaaagatatc tgg                43
```

METHODS AND COMPOSITIONS FOR SELECTION OF FUNCTIONAL OLIGONUCLEOTIDES

RELATED APPLICATIONS

This application is a continuation of International Patent Application No. PCT/IB2018/000418, filed Mar. 30, 2018, which claims the benefit of priority to U.S. Provisional Patent Application Ser. No. 62/478,993, filed Mar. 30, 2017, which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Jul. 30, 2018, is named ANB-001_25_SL.txt and is 2,065 bytes in size.

BACKGROUND

Aptamers are short, single-stranded nucleic acid oligomers that can bind to a specific target molecule. Aptamers are typically selected from a large random pool of oligonucleotides in an iterative process. More recently, aptamers have been successfully selected in cells, in-vivo and in-vitro.

The selection of aptamers, their structure-function relationship, and their mechanisms of action are all poorly-understood. Although more than 100 aptamer structures have been solved and reported, almost no recurring structural motifs have been identified.

A variety of different aptamer selection processes have been described for identifying aptamers capable of binding to a particular target. However, the ability to rapidly and conveniently identify aptamers able to mediate a desirable functional effect on a target of interest would have a profound impact on aptamer therapeutics.

SUMMARY

Provided herein are compositions and methods related to the identification of aptamers that bind to and/or mediate a functional effect on a target (e.g., a target cell or a target molecule). For example, in certain embodiments, provided herein are flow cells (e.g., flow cells for an Illumina sequencing instrument or a Polonator sequencing instrument) comprising within its flow chamber a plurality of immobilized aptamer clusters (e.g., from an aptamer library described herein) and, optionally, one or more target cells (e.g., cancer cells, immune cells, etc.) and/or a detectable indicator of cellular function (e.g., a fluorescent indicator of apoptosis, cell proliferation, gene or protein expression, etc.). In certain embodiments, provided herein are methods of using such an aptamer cluster-containing flow cell to identify functional aptamers from an aptamer library (e.g., in a sequencing instrument, such as an Illumina sequencing instrument).

In certain aspects, provided herein are methods for identifying one or more aptamers that specifically bind to a target (e.g., a target cell, a target virus, a target protein, a topographic feature on a cell). In some embodiments, the methods comprise (i) contacting a plurality of aptamer clusters immobilized on a surface (e.g., a flow cell surface) with the target; and (ii) identifying immobilized aptamer clusters that bind to the target. In certain embodiments, the methods further comprise performing a wash step after step (i) to remove unbound target from surface (e.g., a flow cell surface). In some embodiments, the target is detectably labeled (e.g., fluorescently labeled).

In some aspects, provided herein are methods for identifying one or more aptamers that modulate a property of a cell (e.g., a prokaryotic cell or a eukaryotic cell). In some embodiments, the methods comprise (i) contacting a plurality of aptamer clusters immobilized on a surface with the cell; and (ii) identifying the immobilized aptamer clusters that modulate the property of the cell (e.g., cell viability, cell proliferation, gene expression, cell morphology, etc.). In some embodiments, the methods further comprise performing a wash step after step (i) to remove unbound target from surface (e.g., a flow cell surface). In some embodiments, the cell comprises a detectable label (e.g., a fluorescent dye, such as a calcium sensitive dye, a cell tracer dye, a lipophilic dye, a cell proliferation dye, a cell cycle dye, a metabolite sensitive dye, a pH sensitive dye, a membrane potential sensitive dye, a mitochondrial membrane potential sensitive dye, or a redox potential dye). In some embodiments, a change in the property of the cell causes a change in the properties of the detectable label which are detected in order to identify the immobilized aptamer clusters that modulate the property of the cell.

In some aspects, provided herein are methods for identifying one or more aptamers that possess a functional property (e.g., an enzymatic property) that modulates a target (e.g., a target molecule, such as a target protein). In some embodiments, the methods comprise (i) contacting a plurality of aptamer clusters immobilized on a surface with the target; and (ii) identifying the immobilized aptamer clusters that modulate the target (e.g., that cleave the target, that induce a chemical or structural change on the target, etc.). In some embodiments, the methods further comprise performing a wash step after step (i) to remove unbound target from flow cell.

In certain embodiments, the methods further comprise the generation of the immobilized aptamer clusters. In some embodiments, the immobilized aptamer clusters are generated by: (a) immobilizing a plurality of aptamers (e.g., from an aptamer library) on the surface; and (b) amplifying the plurality of immobilized aptamers locally on the flow cell surface (e.g., via bridge PCR amplification or rolling circle amplification) to form the plurality of immobilized aptamer clusters. In some embodiments, the methods further comprise removing the complementary strands from the immobilized aptamer clusters to provide single stranded immobilized aptamer clusters. In certain embodiments, the immobilized aptamer clusters are sequenced following step (b) (e.g., using Illumina sequencing or Polonator sequencing). In some embodiments, the immobilized aptamer clusters are generated by printing aptamer clusters (e.g., from an aptamer library) directly on the surface. In some embodiments, the methods comprise the generation of the aptamer library (e.g., through chemical nucleic acid synthesis).

In certain aspects, provided herein are compositions comprising aptamer clusters (e.g., a clustered aptamer library). In certain embodiments, the aptamer clusters are immobilized on a solid support (e.g., a flow cell). In certain embodiments, the composition further comprises a target (e.g., a target cell, a target molecule, a target protein). In certain embodiments, the composition further comprises a detectable label (e.g., a fluorescent dye, such as a calcium sensitive dye, a cell tracer dye, a lipophilic dye, a cell proliferation dye, a cell cycle dye, a metabolite sensitive dye, a pH sensitive dye, a membrane potential sensitive dye, a mitochondrial membrane potential sensitive dye, or a redox potential dye). In some embodiments the composition comprises $10^4$-$10^9$ aptamer clusters (e.g., at least about $10^4$, $5\times10^4$, $10^5$, $5\times10^5$, $10^6$, $5\times10^5$, $10^6$, $5\times10^6$, $10^7$, $5\times10^7$, or $10^8$ aptamer clusters. In some embodiments, each cluster in the library contains $10^3$-$10^6$) of aptamers (e.g., at least about $10^3$, $5\times10^3$, $10^4$, $5\times10^4$, $10^5$, $5\times10^5$ aptamers per cluster.

DETAILED DESCRIPTION

General

Figure 1:
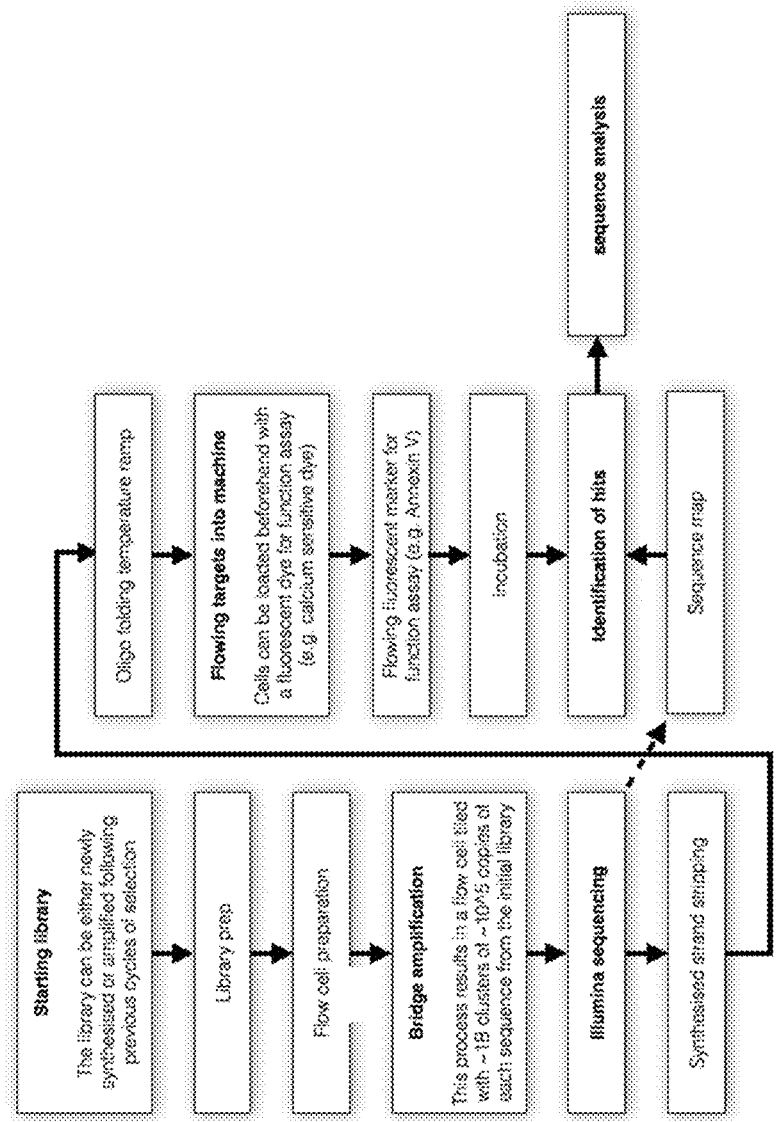
FIG. 1 is a schematic diagram of aptamer library synthesis, sequencing and target identification work flow according to certain embodiments described herein.
Figure 2:
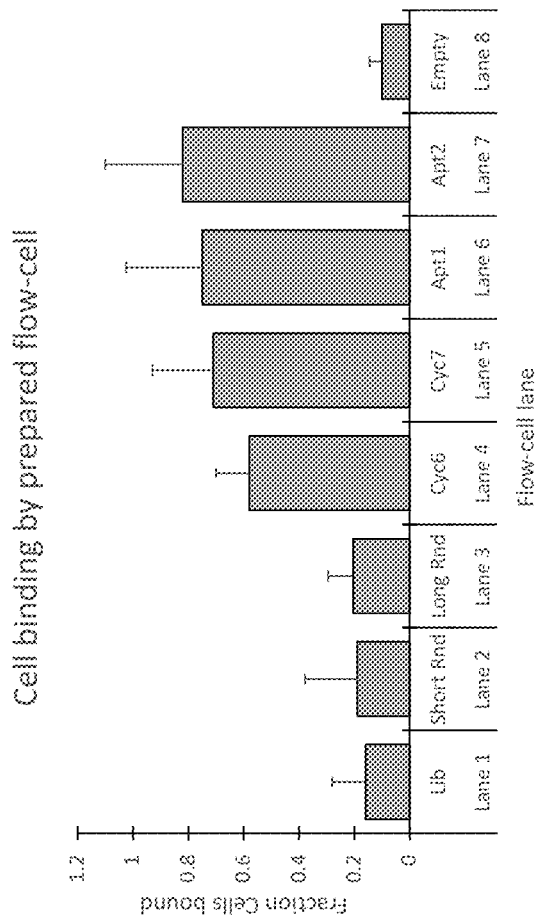
FIG. 2 is a bar graph showing the binding of target cells (Hana cells) to a library of aptamers (Lib), short or long aptamers of random sequence, aptamer outputs of SELEX selection process for the specific target cells cycles 6 and 7 (Cyc6 and Cyc7 respectively), specific aptamer sequences from SELEX selection process (Apt1 and Apt2), and an empty lane (empty) on a Illumina GAIIx flow-cell. Cells were run down flow cell lanes, and bound cells counted (bound vs. unbound, expressed as fraction, 1=100% of cells).

Provided herein are methods and composition related to the identification of aptamers that bind to and/or mediate a functional effect on a target (e.g., a target cell or a target molecule). In certain embodiments the methods comprise contacting the target to a plurality of aptamer clusters immobilized on a surface. Thus, in some embodiments, the method comprises flowing a solution comprising the target across the surface of a flow cell to which clusters of aptamers have been immobilized and detecting which aptamer clusters bind to, interact with and/or mediate a functional effect on the target.

In certain embodiments, the sequence of each immobilized aptamer cluster is known and/or determined, for example, by sequencing the aptamer clusters or by printing aptamers of known sequences onto predetermined positions of the surface. Thus, by determining the position on the surface at which the target binds to, interacts with and/or is modulated by an aptamer cluster, the relevant effect can be associated with the aptamer sequence at that position.

For example, in some embodiments, aptamers that bind to a target are identified by running a composition comprising a target that comprises a detectable label (e.g., a fluorescent label) across a surface to which aptamer clusters of known sequences are immobilized at known positions. The positions on the surface at which the target is retained are determined (e.g., using fluorescent microscopy), indicating that the aptamers immobilized at those positions bind to the target.

In certain embodiments, aptamers that functionally modulate a target are identified by running a composition comprising a target that comprises a detectable label indicative of the function being modulated (e.g., a fluorescent dye, such as a calcium sensitive dye, a cell tracer dye, a lipophilic dye, a cell proliferation dye, a cell cycle dye, a metabolite sensitive dye, a pH sensitive dye, a membrane potential sensitive dye, a mitochondrial membrane potential sensitive dye, or a redox potential dye) across a surface to which aptamer clusters of known sequences are immobilized at known positions. The positions on the surface at which the detectable label indicates that the target is modulated are determined (e.g., using fluorescent microscopy), indicating that the aptamers immobilized at those positions are able to modulate the target.

In certain aspects, also provided herein are methods and compositions related to the creation of immobilized of aptamer clusters on a surface. In some embodiments, aptamers (e.g., from an aptamer library disclosed herein) are immobilized onto a surface, such as a flow cell surface. In some embodiments, a localized amplification process, such as bridge amplification or rolling circle amplification, is then performed to generate aptamer clusters. The aptamer clusters can then be sequenced (e.g., by Illumina sequencing or Polonator sequencing) in order to associate the sequence of each aptamer cluster with a position on the surface. The complementary strands can be stripped in order to generate single-stranded aptamer clusters. The surface (e.g., flow cell) is then ready for use in an aptamer identification method provided herein.

Conveniently, in certain embodiments, all the steps in the methods provided herein can be performed in an Illumina sequencing instrument, such as an Illumina GAIIx instrument.

In certain aspects, provided herein are compositions comprising aptamer clusters (e.g., a clustered aptamer library generated during the performance of a method provided herein). In certain embodiments, the aptamer clusters are immobilized on a solid support (e.g., a flow cell). In certain embodiments, the composition further comprises a target (e.g., a target cell, a target molecule, a target protein). In certain embodiments, the composition further comprises a detectable label (e.g., a fluorescent dye, such as a calcium sensitive dye, a cell tracer dye, a lipophilic dye, a cell proliferation dye, a cell cycle dye, a metabolite sensitive dye, a pH sensitive dye, a membrane potential sensitive dye, a mitochondrial membrane potential sensitive dye, or a redox potential dye). In some embodiments the composition comprises $10^4$-$10^9$ aptamer clusters (e.g., at least about $10^4$, $5 \times 10^4$, $10^5$, $5 \times 10^5$, $10^6$, $5 \times 10^6$, $10^7$, $5 \times 10^7$, or $10^8$ aptamer clusters. In some embodiments, each cluster in the library contains $10^3$-$10^6$) of aptamers (e.g., at least about $10^3$, $5 \times 10^3$, $10^4$, $5 \times 10^4$, $10^5$, $5 \times 10^5$ aptamers per cluster.

In some embodiments, the target can be a cell of any type (e.g. prokaryotic cell, such as a bacterium, or a eukaryotic cell, such as a mammalian cell), a virus, a protein, and/or a particle. In some embodiments, the particle is attached to the target.

In some embodiments, the detectable label is a fluorescent reporter of function. In some embodiments the fluorescent reporter of function is a cell death reporter, a redox potential reporter, a membrane integrity reporter. In some embodiments, the fluorescent reporter of function is a virus reporter, such as a capsid integrity reporter (e.g., a reporter for measuring the capsid integrity and or functions of a virus). In some embodiments, the fluorescent reporter of function is a protein reporter, such as a protein integrity reporter (i.e., a reporter for measuring a protein's structural integrity and stability) or a protein denaturation reporter (i.e., a reporter to detect protein denaturation.

Examples of cell death reporters are 7-AAD, and Annexin V fluorophore. In certain embodiments, the target is linked to, bound by or comprises a detectable label that allows for the detection of a biological or chemical effect on the target. In some embodiments, the detectable label is a fluorescent dye. Non-limiting examples of fluorescent dyes include, but are not limited to, a calcium sensitive dye, a cell tracer dye, a lipophilic dye, a cell proliferation dye, a cell cycle dye, a metabolite sensitive dye, a pH sensitive dye, a membrane potential sensitive dye, a mitochondrial membrane potential sensitive dye, and a redox potential dye. In one embodiment, the target is labeled with a calcium sensitive dye, a cell tracer dye, a lipophilic dye, a cell proliferation dye, a cell cycle dye, a metabolite sensitive dye, a pH sensitive dye, a membrane potential sensitive dye, a mitochondrial membrane potential sensitive dye, or a redox potential dye.

In certain embodiments, the target is labeled with an activation associated marker, an oxidative stress reporter, an angiogenesis marker, an apoptosis marker, an autophagy marker, a cell viability marker, or a marker for ion concentrations. In yet another embodiment, the target is labeled with an activation associated marker, an oxidative stress reporter, an angiogenesis marker, an apoptosis marker, an autophagy marker, a cell viability marker, or a marker for ion concentrations prior to exposure of aptamers to the target.

In some embodiments, the target cell is labeled with a calcium sensitive dye, a cell tracer dye, a lipophilic dye, a cell proliferation dye, a cell cycle dye, a metabolite sensitive dye, a pH sensitive dye, a membrane potential sensitive dye, a mitochondrial membrane potential sensitive dye, or a redox potential dye. In certain embodiments, the target cell is labeled with an activation associated marker, an oxidative stress reporter, an angiogenesis marker, an apoptosis marker, an autophagy marker, a cell viability marker, or a marker for ion concentrations. In yet another embodiment, target cell is labeled with an activation associated marker, an oxidative stress reporter, an angiogenesis marker, an apoptosis marker, an autophagy marker, a cell viability marker, or a marker for ion concentrations prior to exposure of aptamers to the cell. In some embodiments, the target cell is labeled after to exposure of aptamers to the target. In one embodiment, the target cell is labeled with a fluorescently-labeled antibody or antigen-binding fragment thereof, annexin V, a fluorescently-labeled fusion protein, a fluorescently-labeled sugar, or fluorescently labeled lectin. In one embodiment, the target cell is labeled with a fluorescently-labeled antibody or antigen-binding fragment thereof, annexin V, a fluorescently-labeled fusion protein, a fluorescently-labeled sugar, or fluorescently labeled lectin after exposure of aptamers to the cell.

In some embodiments the aptamer clusters are immobilized on a flow cell (e.g., a flow cell is used for image-based DNA sequencing, such as, Illumina instrument flow cell and/or Polonator sequencer flow cell). In certain embodiments, the flow cell can be made of any material. In some embodiments the flow cell is made of plastic, glass, polymer, or metal. In some embodiments, the flow cell is a plate, a tray, or a chip. In some embodiments, the flow cell contains between its floor and ceiling one or more of the following: air, water, aqueous buffer, culture medium, serum, patient-derived sample (e.g. blood, plasma, serum, urine), matrix (e.g. gel), a polymer, and/or a protein (e.g. collage, or patient-derived extracellular matrix). In some embodiments, the flow cell contains targets (e.g., target cells). In some embodiments, the flow cell (e.g. its floor and/or its ceiling) is coated with a blocker, such as, a polymer, a protein, an oligo, a lipid, and/or a chemical group. In some embodiments, the flow cell contains an anchor of any length to bind the target at proximity to clusters. In some embodiments, the anchor is a polymer, a protein, an oligo, a lipid, and/or a chemical group.

In some embodiments, the aptamer clusters are arranged randomly in the flow cell. In other embodiments, the aptamer clusters are arranged according to a specific pattern in the flow cell. In some embodiments, the flow cell is fixed at any stage. In some embodiments, the composition further comprises a fixative. In some embodiments, the flow cell is used for iterative process of oligo selection. In other embodiments, the flow cell is used in non-iterative process of oligo selection.

In certain embodiments, the target is labeled with an activation associated marker, an oxidative stress reporter, an angiogenesis marker, an apoptosis marker, an autophagy marker, a cell viability marker, or a marker for ion concentrations. In yet another embodiment, the target is labeled with an activation associated marker, an oxidative stress reporter, an angiogenesis marker, an apoptosis marker, an autophagy marker, a cell viability marker, or a marker for ion concentrations prior to exposure of aptamers to the target.

Definitions

For convenience, certain terms employed in the specification, examples, and appended claims are collected here.

The articles "a" and "an" are used herein to refer to one or to more than one (e.g., to at least one) of the grammatical object of the article. By way of example, "an element" means one element or more than one element.

As used herein, the term "aptamer" refers to a short (e.g., less than 200 bases), single stranded nucleic acid molecule (ssDNA and/or ssRNA) able to specifically bind to a protein or peptide target or to a topographic feature on a target cell.

As used herein, the term "aptamer cluster" refers to a collection of locally immobilized aptamers (e.g., at least 10) of identical sequence.

The term "binding" or "interacting" refers to an association, which may be a stable association, between two molecules, e.g., between an aptamer and target, e.g., due to, for example, electrostatic, hydrophobic, ionic and/or hydrogen-bond interactions under physiological conditions.

As used herein, two nucleic acid sequences "complement" one another or are "complementary" to one another if they base pair one another at each position.

As used herein, two nucleic acid sequences "correspond" to one another if they are both complementary to the same nucleic acid sequence.

The term "modulation", when used in reference to a functional property or biological activity or process (e.g., enzyme activity or receptor binding), refers to the capacity to either up regulate (e.g., activate or stimulate), down regulate (e.g., inhibit or suppress) or otherwise change a quality of such property, activity, or process. In certain instances, such regulation may be contingent on the occurrence of a specific event, such as activation of a signal transduction pathway, and/or may be manifest only in particular cell types.

As used herein, "specific binding" refers to the ability of an aptamer to bind to a predetermined target. Typically, an aptamer specifically binds to its target with an affinity corresponding to a $K_D$ of about $10^{-7}$ M or less, about $10^{-8}$ M or less, or about $10^{-9}$ M or less and binds to the target with a $K_D$ that is significantly less (e.g., at least 2 fold less, at least 5 fold less, at least 10 fold less, at least 50 fold less, at least 100 fold less, at least 500 fold less, or at least 1000 fold less) than its affinity for binding to a non-specific and unrelated target (e.g., BSA, casein, or an unrelated cell, such as an HEK 293 cell or an *E. coli* cell).

As used herein, the Tm or melting temperature of two oligonucleotides is the temperature at which 50% of the oligonucleotide/targets are bound and 50% of the oligonucleotide target molecules are not bound. Tm values of two oligonucleotides are oligonucleotide concentration dependent and are affected by the concentration of monovalent, divalent cations in a reaction mixture. Tm can be determined empirically or calculated using the nearest neighbor formula, as described in Santa Lucia, J. PNAS (USA) 95:1460-1465 (1998), which is hereby incorporated by reference.

The terms "polynucleotide" and "nucleic acid" are used herein interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, synthetic polynucleotides, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified, such as by conjugation with a labeling component.

Aptamer Libraries

In certain embodiments, the methods and compositions provided herein relate to the identification of aptamers having desired properties from among the aptamers present in an aptamer library. As used herein, an aptamer library is a collection of nucleic acid molecules (e.g., DNA and/or RNA) having distinct sequences (e.g., at least $10^2$, $10^3$, $10^4$, $10^5$, $10^6$ or $10^7$ distinct sequences) and wherein at least a subset of the nucleic acid molecules is structured such that they are capable of specifically binding to a target protein, peptide, or cellular topographic feature. In some embodiments, any library of potential aptamers can be used in the methods and compositions provided herein.

In some embodiments, the aptamer library used in the methods and compositions provided herein comprises, consists of and/or consists essentially of nucleic acid molecules (e.g., DNA and/or RNA) having a sequence according to Formula (I):

$$P1\text{-}R\text{-}P2 \qquad (I),$$

wherein P1 is a 5' primer site sequence of about 10 to 100 bases in length, about 10 to 50 bases in length, about 10 to 30 bases in length, about 15 to 50 bases in length or about 15 to 30 bases in length; P2 is a 3' primer site sequence of about 10 to 100 bases in length, about 10 to 50 bases in length, about 10 to 30 bases in length, about 15 to 50 bases in length or about 15 to 30 bases in length; and R is a sequence comprising randomly positioned bases of about at least 10, 15, 20, 25, 30, 35, 40, 45, 50, 55, 60, 65, 70, 75 or 80 bases in length and/or no more than about 120, 115, 110, 105, 100, 95, 90, 85, 80, 75, 70, 65, 60, 55 or 50 bases in length.

In one embodiment, R is a sequence comprising about 25% A. In another embodiment, R is a sequence comprising about 25% T. In another embodiment, R is a sequence comprising about 25% G. In another embodiment, R is a sequence comprising about 25% C. In yet another embodiment, R is a sequence comprising about 25% A, about 25% T, about 25% G, and about 25% C.

In some embodiments, the aptamer library used in the methods and compositions provided herein comprises, consists of and/or consists essentially of nucleic acid molecules (DNA and/or RNA) having a sequence according to Formula (I):

$$P1\text{-}R''\text{-}P2 \qquad (I),$$

wherein P1 is a 5' primer site sequence of about 10 to 100 bases in length, about 10 to 50 bases in length, about 10 to 30 bases in length, about 15 to 50 bases in length or about 15 to 30 bases in length; P2 is a 3' primer site sequence of about 10 to 100 bases in length, about 10 to 50 bases in length, about 10 to 30 bases in length, about 15 to 50 bases in length or about 15 to 30 bases in length; and R" is a sequence of about at least 10, 15, 20, 25, 30, 35, 40, 45, 50, 55, 60, 65, 70, 75 or 80 bases in length and/or no more than about 120, 115, 110, 105, 100, 95, 90, 85, 80, 75, 70, 65, 60, 55 or 50 bases in length comprising randomly positioned bases from a biased mixture or any combination of random strings with repetitive or biased strings.

Figure 4:
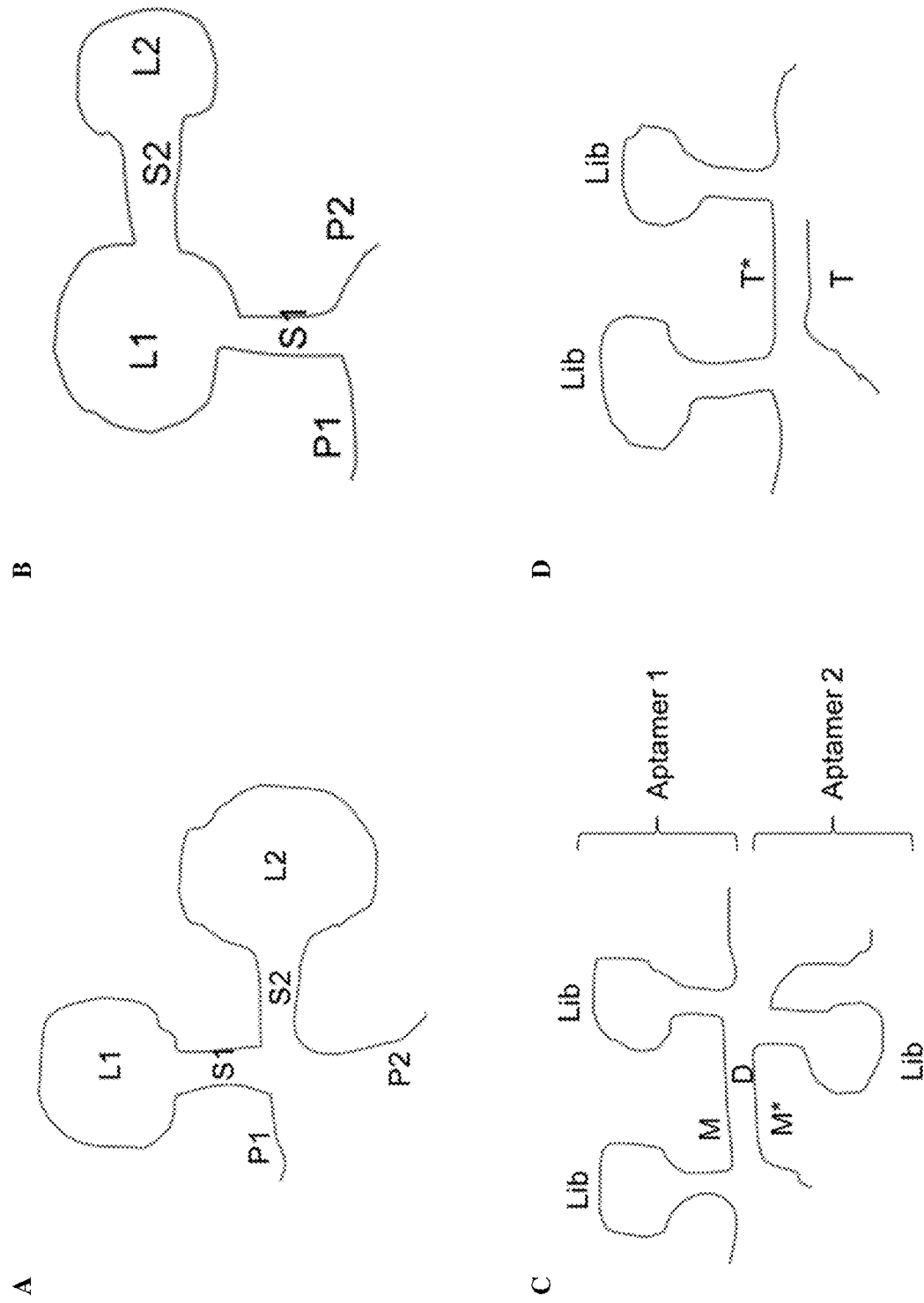
FIG. 4 is a schematic representation of certain aptamer structures according to certain exemplary embodiments provided herein.
Figure 5:
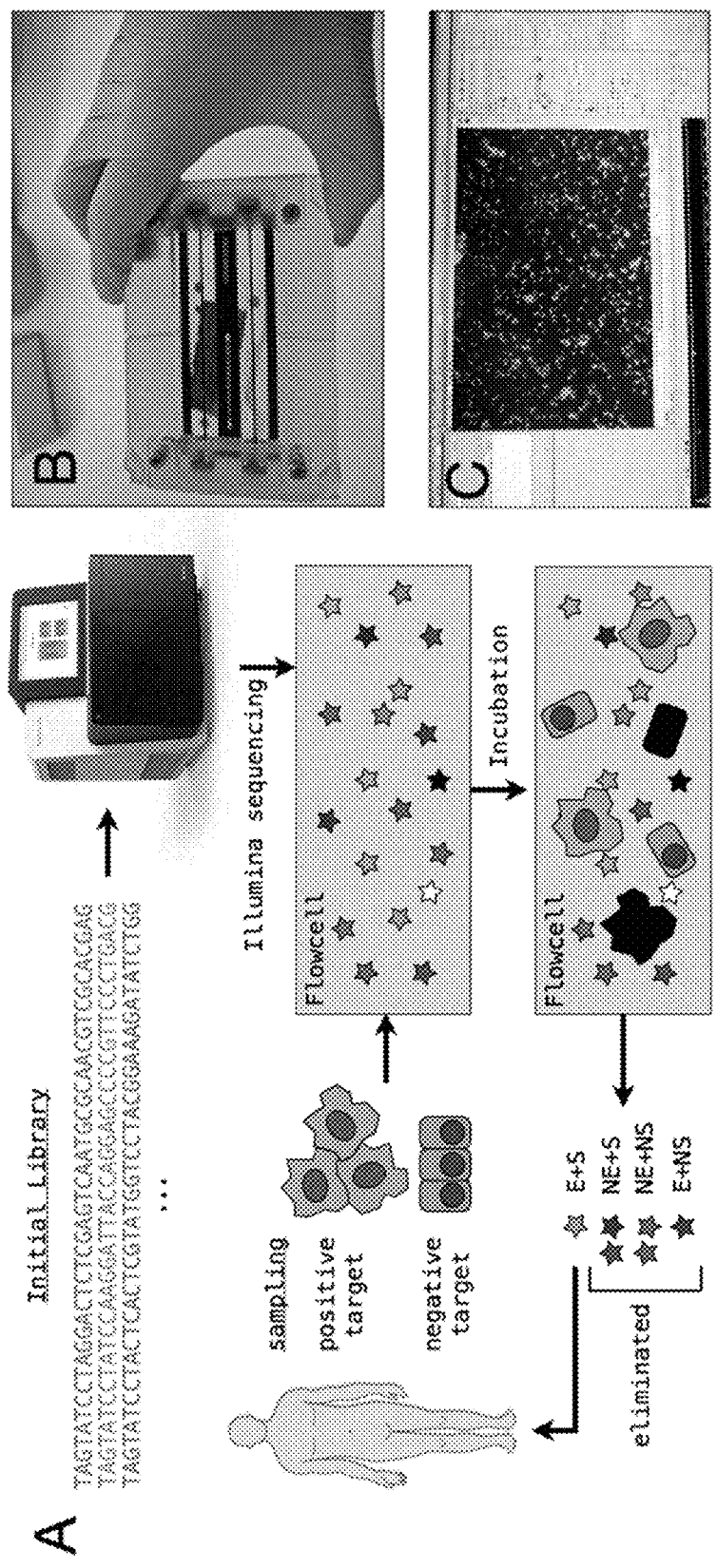
FIG. 5 includes three panels and illustrates an exemplary aptamer identification method according to certain embodiments disclosed herein. Panel A, is a schematic representation of a flow-cell based aptamer detection method. An initial aptamer library (SEQ ID NOS 5-7, respectively, in order of appearance) is sequenced and a flow-cell is generated in which aptamers from the library are clustered at a unique coordinates. Positive targets (e.g. tumor biopsy cells) and negative targets (e.g. peripheral bloods) are labeled with fluorescent indicators for one or more biological effects (e.g. apoptosis) and introduced into different lanes of the flow-cell on which the aptamer clusters are immobilized. Following an incubation, fluorescence is detected and associated with a position on the flow cell on which an aptamer cluster is immobilized. Aptamers are scored based on effectiveness yes/no (Effect/No Effect) and selectivity yes/no (Selective/Not Selective). The highest scored oligos (E+S) are synthesized and validated. Panel B shows a photograph of a flow-cell following sequencing, held inside a custom-built adapter for a screening fluorescent microscope. Panel C is a screenshot of a fluorescent microscope image obtained during performance of an embodiment of the claimed method showing target cells following incubation, with apoptotic cells producing a positive signal.

In some embodiments, the aptamer library used in the methods and compositions provided herein comprises, consists of and/or consists essentially of nucleic acid molecules (DNA and/or RNA) having a sequence according to Formula II (an exemplary schematic representation is provided in FIG. 4A), $$P1\text{-}S1\text{-}L1\text{-}S1^*\text{-}S2\text{-}L2\text{-}S2^*\text{-}P2 \qquad (II),$$

wherein:
P1 is a 5' primer site sequence of about 10 to 100 bases in length, about 10 to 50 bases in length, about 10 to 30 bases in length, about 15 to 50 bases in length or about 15 to 30 bases in length; P2 is a 3' primer site sequence of about 10 to 100 bases in length, about 10 to 50 bases in length, about 10 to 30 bases in length, about 15 to 50 bases in length or about 15 to 30 bases in length; S1 and S2 are each independently a stem region sequence of at least one base (e.g., of about 4 to 40 bases in length or 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 bases in length); S1* is a complementary sequence to S1; S2* is a complementary sequence to S2; L1 and L2 are each independently a Loop region sequence of at least one base (e.g., of about 1 to 50 bases in length or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 bases in length); and S1-L1-S1*-S2-L2-S2* is collectively about at least 10, 15, 20, 25, 30, 35, 40, 45, 50, 55, 60, 65, 70, 75 or 80 bases in length and/or no more than about 120, 115, 110, 105, 100, 95, 90, 85, 80, 75, 70, 65, 60, 55 or 50 bases in length.

In some embodiments, the aptamer library used in the methods and compositions provided herein comprises, consists of and/or consists essentially of nucleic acid molecules (DNA and/or RNA) having a sequence according Formula III (an exemplary schematic representation is provided in FIG. 4B):

P1-S1-L1-S2-L2-S2*-L1-S1*-P2 (III), wherein:

P1 is a 5' primer site sequence of about 10 to 100 bases in length, about 10 to 50 bases in length, about 10 to 30 bases in length, about 15 to 50 bases in length or about 15 to 30 bases in length; P2 is a 3' primer site sequence of about 10 to 100 bases in length, about 10 to 50 bases in length, about 10 to 30 bases in length, about 15 to 50 bases in length or about 15 to 30 bases in length;

S1 and S2 are each independently a stem region sequence of at least one base (e.g., of about 4 to 40 bases in length or 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 bases in length); S1* is a complementary sequence to S1; S2* is a complementary sequence to S2;

L1 and L2 are each independently a Loop region sequence of at least one base (e.g., of about 1 to 50 bases in length or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 bases in length); and S1-L1-S2-L2-S2*-L1-S1* is collectively about at least 10, 15, 20, 25, 30, 35, 40, 45, 50, 55, 60, 65, 70, 75 or 80 bases in length and/or no more than about 120, 115, 110, 105, 100, 95, 90, 85, 80, 75, 70, 65, 60, 55 or 50 bases in length.

In some embodiments, the aptamer library used in the methods and compositions provided herein comprises, consists of and/or consists essentially of nucleic acid molecules (DNA and/or RNA) having a sequence according Formula IV (an exemplary schematic representation is provided in FIG. 4C):

P1-Lib-M1/M2-D-M1/M2*-Lib-P2 (IV), wherein:

P1 is a 5' primer site sequence of about 10 to 100 bases in length, about 10 to 50 bases in length, about 10 to 30 bases in length, about 15 to 50 bases in length or about 15 to 30 bases in length; P2 is a 3' primer site sequence of about 10 to 100 bases in length, about 10 to 50 bases in length, about 10 to 30 bases in length, about 15 to 50 bases in length or about 15 to 30 bases in length;

Lib is sequence having a formula selected from: (i) R; (ii) R"; (iii) S1-L1-S1*-S2-L2-S2*; and (iv) S1-L1-S2-L2-S2*-L1-S1*;

R is a sequence comprising randomly positioned bases of about at least 10, 15, 20, 25, 30, 35, 40, 45, 50, 55, 60, 65, 70, 75 or 80 bases in length and/or no more than about 120, 115, 110, 105, 100, 95, 90, 85, 80, 75, 70, 65, 60, 55 or 50 bases in length;

R" is a sequence of about at least 10, 15, 20, 25, 30, 35, 40, 45, 50, 55, 60, 65, 70, 75 or 80 bases in length and/or no more than about 120, 115, 110, 105, 100, 95, 90, 85, 80, 75, 70, 65, 60, 55 or 50 bases in length comprising randomly positioned bases from a biased mixture or any combination of random strings with repetitive or biased strings; S1 and S2 are each independently a stem region sequence of at least one base (e.g., of about 4 to 40 bases in length or 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 bases in length); S1* is a complementary sequence to S1; S2* is a complementary sequence to S2;

L1 and L2 are each independently a Loop region sequence of at least one base (e.g., of about 1 to 50 bases in length or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 bases in length);

wherein S1-L1-S1*-S2-L2-S2* is collectively about at least 10, 15, 20, 25, 30, 35, 40, 45, 50, 55, 60, 65, 70, 75 or 80 bases in length and/or no more than about 120, 115, 110, 105, 100, 95, 90, 85, 80, 75, 70, 65, 60, 55 or 50 bases in length;

D is a spacer sequence comprising at least one base (e.g., of about 1 to 20 bases in length or 1, 2, 3, 4, 5, 6, 7, 8, 9, 10, 11, 12, 13, 14, 15, 16, 17, 18, 19 or 20 bases in length);

M1 is a multimer-forming domain sequence of about 10 to 18 bases in length or 10, 11, 12, 13, 14, 15, 16, 17 or 18 bases in length that enables a strand of the sequence to interact with another strand that contains a complementary domain; and M2 is a complementary domain of M1 comprising a strand that interacts with a strand of the M1 sequence.

In some embodiments, the aptamer library used in the methods and compositions provided herein comprises, consists of and/or consists essentially of nucleic acid molecules (DNA and/or RNA) having a sequence according Formula V (an exemplary schematic representation is provided in FIG. 4D):

P1-Lib-T*-Lib-P2 (V), wherein:

P1 is a 5' primer site sequence of about 10 to 100 bases in length, about 10 to 50 bases in length, about 10 to 30 bases in length, about 15 to 50 bases in length or about 15 to 30 bases in length; P2 is a 3' primer site sequence of about 10 to 100 bases in length, about 10 to 50 bases in length, about 10 to 30 bases in length, about 15 to 50 bases in length or about 15 to 30 bases in length;

Lib is sequence having a formula selected from: (i) R; (ii) R"; (iii) S1-L1-S1*-S2-L2-S2*; and (iv) S1-L1-S2-L2-S2*-L1-S1*;

R is a sequence comprising randomly positioned bases of about at least 10, 15, 20, 25, 30, 35, 40, 45, 50, 55, 60, 65, 70, 75 or 80 bases in length and/or no more than about 120, 115, 110, 105, 100, 95, 90, 85, 80, 75, 70, 65, 60, 55 or 50 bases in length;

R" is a sequence of about at least 10, 15, 20, 25, 30, 35, 40, 45, 50, 55, 60, 65, 70, 75 or 80 bases in length and/or no more than about 120, 115, 110, 105, 100, 95, 90, 85, 80, 75, 70, 65, 60, 55 or 50 bases in length comprising randomly positioned bases from a biased mixture or any combination of random strings with repetitive or biased strings;

S1 and S2 are each independently a stem region sequence of at least one base (e.g., of about 4 to 40 bases in length or 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 bases in length); S1* is a complementary sequence to S1; S2* is a complementary sequence to S2;

L1 and L2 are each independently a Loop region sequence of at least one base (e.g., of about 1 to 50 bases in length or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 bases in length);

wherein S1-L1-S1*-S2-L2-S2* is collectively about at least 10, 15, 20, 25, 30, 35, 40, 45, 50, 55, 60, 65, 70, 75 or 80 bases in length and/or no more than about 120, 115, 110, 105, 100, 95, 90, 85, 80, 75, 70, 65, 60, 55 or 50 bases in length;

T is a second strand bound by Watson/Crick or Hoogsteen base pairing to any part of the Lib sequence or T*, wherein the strand optionally contains unpaired domains on its 5' and 3' ends (e.g., to facilitate attachment of a functional moiety to the aptamer); and T* is a dedicated domain sequence (e.g., of about 4 to 40 bases in length or 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 bases in length).

In some embodiments of the Formulae above, R is randomly positioned bases from any random mixture (e.g., for canonical bases, 25% A, 25% T, 25% G, 25% C) of about at least 10, 15, 20, 25, 30, 35, 40, 45, 50, 55, 60, 65, 70, 75 or 80 bases in length and/or no more than about 120, 115, 110, 105, 100, 95, 90, 85, 80, 75, 70, 65, 60, 55 or 50 bases in length.

In one embodiment of the Formulae above, R is a sequence comprising about 25% A. In another embodiment, R is a sequence comprising about 25% T. In another embodiment, R is a sequence comprising about 25% G. In another embodiment, R is a sequence comprising about 25% C. In yet another embodiment, R is a sequence comprising about 25% A, about 25% T, about 25% G, and about 25% C.

In some embodiments of the Formulae above, R" is a sequence comprising comprises randomly positioned bases from a biased mixture (e.g., for canonical bases, any mixture deviating from 25% per base). In some embodiments, R" is a sequence that comprises about 0%, 5%, 10%, 15%, 20%, 25%, 30%, 35%, 40%, 45%, 50%, 55%, 60%, 65%, 70% or 75% A. In some embodiments, R" is a sequence that comprises about 0%, 5%, 10%, 15%, 20%, 25%, 30%, 35%, 40%, 45%, 50%, 55%, 60%, 65%, 70% or 75% T. In some embodiments, R" is a sequence that comprises about 0%, 5%, 10%, 15%, 20%, 25%, 30%, 35%, 40%, 45%, 50%, 55%, 60%, 65%, 70% or 75% C. In some embodiments, R" is a sequence that comprises about 0%, 5%, 10%, 15%, 20%, 25%, 30%, 35%, 40%, 45%, 50%, 55%, 60%, 65%, 70% or 75% G. In some embodiments, R" is a sequence that comprises any combination of random strings (string is any sequence including a single base) with repetitive or biased strings.

In some embodiments of the Formulae above, R" is randomly positioned bases from a biased mixture (e.g., for canonical bases, any mixture deviating from 25% per base); or any combination of random strings (string is any sequence including a single base) with repetitive or biased strings of about at least 10, 15, 20, 25, 30, 35, 40, 45, 50, 55, 60, 65, 70, 75 or 80 bases in length and/or no more than about 120, 115, 110, 105, 100, 95, 90, 85, 80, 75, 70, 65, 60, 55 or 50 bases in length.

In some embodiments of the Formulae above, S1 is a stem region sequence of at least 1 base or more. In other embodiments, S1 is a stem region sequence of between about 4 to 40 bases in length or 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 bases in length.

In some embodiments of the Formulae above, S2 is a stem region sequence of at least 1 base or more. In other embodiments, S2 is a stem region sequence of between about 4 to 40 bases in length or 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 bases in length.

In some embodiments of the Formulae above, L1 is a Loop region sequence of at least one base. In other embodiments, L1 is a Loop region sequence of about 1 to 50 bases in length or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 bases in length.

In some embodiments of the Formulae above, L2 is a Loop region sequence of at least one base. In other embodiments, L2 is a Loop region sequence of about 1 to 50 bases in length or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 bases in length.

In some embodiments of the Formulae above, T may include unpaired domains on its 5' and 3' ends, or it may be a padlock tail (e.g., a loop between two domains paired with the library).

The aptamers of the present disclosure may contain any number of stems and loops, and other structures comprised of stems and loops (e.g., hairpins, bulges, etc.). In some embodiments, the loops in the aptamer contain bases implanted in order to form stable loop-loop WC pairing forming a stem which is orthogonal to the main library axis. In other embodiments, two loops in the aptamer together form an orthogonal stem. In yet other embodiments, the loops in the aptamer contain bases implanted in order to form stable Hoogsteen pairing with an existing stem along the main library axis. In other embodiments, the loops in the aptamer can form Hoogsteen pairing with any stem in the aptamer.

In some embodiments of the formulae above, the aptamer sequence further contains one or more multimer-forming domains.

In some embodiments of the formulae above, the aptamer sequence further contains one or more spacers (e.g., of about 1 to 20 bases in length or 1, 2, 3, 4, 5, 6, 7, 8, 9, 10, 11, 12, 13, 14, 15, 16, 17, 18, 19 or 20 bases in length).

The aptamers of the present disclosure can be prepared in a variety of ways. In one embodiment, the aptamers are prepared through chemical synthesis. In another embodiment, the aptamers are prepared through enzymatic synthesis. In one embodiment, the enzymatic synthesis can be carried out using any enzyme that can add nucleotides to elongate a primer, with or without template. In some embodiments, the aptamers are prepared by assembling together k-mers (e.g., k≥2 bases).

In some embodiments, the aptamers of the present disclosure may contain any combination of DNA, RNA, and their natural and/or synthetic analogs. In one embodiment, the aptamer comprises DNA. In one embodiment, the aptamer comprises RNA.

In other embodiments, the aptamers of the present disclosure may contain any modification on the 5' end, 3' end, or internally. Modifications of the aptamers include, but are not limited to, spacers, phosphorylation, linkers, conjugation chemistries, fluorophores, quenchers, photoreactive, and modified bases (e.g., LNA, PNA, UNA, PS, methylation, 2-O-methyl, halogenated, superbases, iso-dN, inverted bases, L-ribose, other sugars as backbone, etc.).

In some embodiments, the aptamers of the present disclosure may be conjugated to external, non-nucleic acid molecules on the 5' end, 3' end, or internally. Non-limiting examples of non-nucleic acid molecules include, but are not limited to. amino acids, peptides, proteins, small molecule drugs, mono- and polysaccharides, lipids, antibodies and antibody fragments, or a combination thereof.

The aptamers of the present disclosure may contain any domain which has a biological function. Non-limiting examples of biological functions of the aptamers described herein include, but are not limited to, acting as templates for RNA transcription, binding to, recognizing, and/or modulating the activity of proteins, binding to transcription factors, specialized nucleic acid structure (e.g., Z-DNA, H-DNA, G-quad, etc.), and acting as an enzymatic substrate for restriction enzymes, specific exo- and endonucleases, recombination sites, editing sites, or siRNA. In one embodiment, the aptamers modulate the activity of at least one protein. In another embodiment, the aptamers inhibit the activity of at least one protein. In yet another embodiment, the aptamers inhibit the activity of at least one protein In other embodiments, the aptamers of the present disclosure may contain any domain for integration into a nucleic acid nanostructure built by any one of several known methods (Shih et al, Nature 427:618-621 (2004); Rothemund, Nature 440:297-302 (2006); Zheng et al, Nature 461:74-77 (2009); Dietz et al, Science 325:725-730 (2009); Wei et al, Nature 485:623-626 (2012); Ke et al, Science 338:1177-1183 (2012); Douglas et al, Science 335: 831-834 (2012), each of which are hereby incorporated by reference). In yet other embodiments, the aptamers of the present disclosure may contain any domain that serves a function in molecular logic and computation (Seelig et al, Science 314:1585-1588 (2006); Macdonald et al, Nano Lett 6:2598-2603 (2006); Qian et al, Nature 475:368-372 (2011); Douglas et al, Science 335:831-834 (2012); Amir et al, Nat Nanotechnol 9:353-357 (2014), each of which is hereby incorporated by reference).

In some embodiments, the aptamers of the present disclosure undergo one or more cycles of negative selection versus a target (e.g., eukaryotic or prokaryotic cell, virus or viral particle, molecule, tissue, or whole organism, in-vivo or ex-vivo). In other embodiments, the aptamers of the present disclosure undergo one or more cycles of positive selection versus a target (e.g., eukaryotic or prokaryotic cell, virus or viral particle, molecule, tissue, or whole organism, in-vivo or ex-vivo).

The aptamers of the present disclosure can be in solution or attached to a solid phase (e.g., surface, particles, resin, matrix, etc.). In some embodiments, the aptamer is attached to a surface. In one embodiment, the surface is a flow cell surface.

In some embodiments, the aptamers of the present disclosure are synthesized in an aptamer library. The aptamer library of the present disclosure can be prepared in a variety of ways. In one embodiment, the aptamer library is prepared through chemical synthesis. In another embodiment, the aptamer library is prepared through enzymatic synthesis. In one embodiment, the enzymatic synthesis can be carried out using any enzyme that can add nucleotides to elongate a primer, with or without template.

In some embodiments, the aptamers synthesized in an aptamer library may contain any combination of DNA, RNA, and their natural and/or synthetic analogs. In one embodiment, the aptamers synthesized in an aptamer library comprise DNA. In one embodiment, the aptamers synthesized in an aptamer library comprise RNA.

In some embodiments, the aptamers synthesized in an aptamer library are a nucleic acid (e.g., DNA, RNA, natural or synthetic bases, base analogs, or a combination thereof) collection of $10^K$ species ($K \geq 2$), with Z copies per species ($1 \leq Z \leq K-1$).

In other embodiments, the aptamers synthesized in an aptamer library of the present disclosure may contain any modification on the 5' end, 3' end, or internally. Modifications of the aptamers include, but are not limited to, spacers, phosphorylation, linkers, conjugation chemistries, fluorophores, quenchers, photoreactive modifications, and modified bases (e.g., LNA, PNA, UNA, PS, methylation, 2-O-methyl, halogenated, superbases, iso-dN, inverted bases, L-ribose, other sugars as backbone).

In some embodiments, the aptamers synthesized in an aptamer library may be conjugated to external, non-nucleic acid molecules on the 5' end, 3' end, or internally. Non-limiting examples of non-nucleic acid molecules include, but are not limited to amino acids, peptides, proteins, small molecule drugs, mono- and polysaccharides, lipids, antibodies and antibody fragments, or a combination thereof.

The aptamers synthesized in an aptamer library may contain any domain which has a biological function. Non-limiting examples of biological functions of the aptamers described herein include, but are not limited to, acting as templates for RNA transcription, binding to, recognizing, and/or modulating the activity of proteins, binding to transcription factors, specialized nucleic acid structure (e.g., Z-DNA, H-DNA, G-quad, etc.), acting as an enzymatic substrate for restriction enzymes, specific exo- and endonucleases, recombination sites, editing sites, or siRNA. In one embodiment, the aptamers synthesized in an aptamer library modulate the activity of at least one protein. In another embodiment, the aptamers synthesized in an aptamer library inhibit the activity of at least one protein. In yet another embodiment, the aptamers synthesized in an aptamer library inhibit the activity of at least one protein In other embodiments, the aptamers synthesized in an aptamer library may contain any domain for integration into a nucleic acid nanostructure built by one of several known methods (Shih et al, Nature 427:618-621 (2004); Rothemund, Nature 440:297-302 (2006); Zheng et al, Nature 461:74-77 (2009); Dietz et al, Science 325:725-730 (2009); Wei et al, Nature 485:623-626 (2012); Ke et al, Science 338:1177-1183 (2012); Douglas et al, Science 335: 831-834 (2012), each of which are hereby incorporated by reference). In yet other embodiments, the aptamers of the present disclosure may contain any domain that serves a function in molecular logic and computation (Seelig et al, Science 314:1585-1588 (2006); Macdonald et al, Nano Lett 6:2598-2603 (2006); Qian et al, Nature 475:368-372 (2011); Douglas et al, Science 335:831-834 (2012); Amir et al, Nat Nanotechnol 9:353-357 (2014), each of which is hereby incorporated by reference)

In some embodiments, the aptamers synthesized in an aptamer library undergo one or more cycles of negative selection versus a target (e.g., eukaryotic or prokaryotic cell, virus or viral particle, molecule, tissue, or whole organism, in-vivo or ex-vivo). In other embodiments, the aptamers of the present disclosure undergo one or more cycles of positive selection versus a target (e.g., eukaryotic or prokaryotic cell, virus or viral particle, molecule, tissue, or whole organism, in-vivo or ex-vivo).

The aptamers synthesized in an aptamer library can be in solution or attached to a solid phase (e.g., surface, particles, resin, matrix, etc.). In some embodiments, the aptamers synthesized in an aptamer library are attached to a surface. In one embodiment, the surface is a flow cell surface.

Immobilized Aptamer Clusters

In certain aspects, provided herein are methods for identifying aptamers that bind to and/or modulate a target by flowing a sample comprising the target across a plurality of aptamer clusters (e.g., clusters of aptamers from the aptamer libraries provided herein) immobilized on a surface. In certain embodiments the surface can be any solid support. In some embodiments, the surface is the surface of a flow cell. In some embodiments, the surface is a slide or chip (e.g., the surface of a gene chip). In some embodiments, the surface is a bead (e.g., a paramagnetic bead).

In certain embodiments, any method known in the art can be used to generate the immobilized aptamer clusters on the surface. In some embodiments, the aptamer clusters are printed directly onto the surface. For example, in some embodiments, the aptamer clusters are printed with fine-pointed pins onto glass slides, printed using photolithography, printed using ink-jet printing, or printed by electrochemistry on microelectrode arrays. In some embodiments, at least about $10^2$, $10^3$, $10^4$, $10^5$, $10^6$ or $10^7$ distinct aptamer clusters are printed onto the surface. In some embodiments, each aptamer cluster comprises at least about 10, 20, 30, 40, 50, 60, 70, 80, 90, 100, 125, 150, 175, 200, 250, 300, 350, 400, 450, 500, 600, 700, 800, 900, 1000, 2000, 3000, 4000, 5000, 10,000, 20,000, 30,000, 40,000, 50,000, 60,000, 70,000, 80,000, 90,000 or 100,000 identical aptamer molecules. Advantageously, direct printing of microarrays allows for aptamers of known sequence to be specifically immobilized at a predetermined position on the surface, so subsequent sequencing may be unnecessary.

In certain embodiments, the surface-immobilized aptamer clusters are generated by first immobilizing aptamers (e.g., from an aptamer library disclosed herein) onto the surface (e.g., wherein the position at which each aptamer is immobilized is random). In some embodiments, at least about $10^2$, $10^3$, $10^4$, $10^5$, $10^6$, $10^7$, $10^8$, $10^9$ or $10^{10}$ distinct aptamers are immobilized onto the surface. Following aptamer immobilization, a localized amplification process (e.g., bridge amplification or rolling circle amplification), is then performed to generate clusters of copies of each immobilized aptamer positioned proximal to the immobilization site of the original immobilized aptamer. In certain embodiments (e.g., embodiments in which rolling circle amplification is performed) the aptamer cluster is housed in a nano-pit or pore on the surface rather than being directly immobilized on the surface. In some embodiments, amplification results in each aptamer cluster comprising at least about 10, 20, 30, 40, 50, 60, 70, 80, 90, 100, 125, 150, 175, 200, 250, 300, 350, 400, 450, 500, 600, 700, 800, 900, 1000, 2000, 3000, 4000, 5000, 10,000, 20,000, 30,000, 40,000, 50,000, 60,000, 70,000, 80,000, 90,000 or 100,000 identical aptamer molecules. In certain embodiments, the aptamer clusters are then sequenced (e.g., by Illumina sequencing or Polonator sequencing) in order to associate the sequence of each aptamer cluster with its position on the surface. If present, complementary strands can be stripped from the aptamer cluster by washing the surface under conditions not amenable to strand hybridization (e.g., due to salt concentration and/or temperature) in order to generate clusters of single-stranded aptamers. The surface (e.g., flow cell) is then ready for use in an aptamer identification method provided herein. In some embodiments, the immobilized aptamer clusters are prepared and/or sequenced on one instrument, and then transferred to a separate instrument for aptamer identification. In other embodiments, the aptamer clusters are prepared and/or sequenced on the same instrument as is used for aptamer identification.

In some embodiments of the methods above, the aptamers or aptamer clusters (e.g., from the aptamer library) comprise an adapter that will bring the aptamers to surface height (e.g., in cases where the surface is not flat, such as in flow cells that include pores). In one embodiment, the aptamers or aptamer clusters are immobilized inside pores on a flow cell surface and adapters are used to bind the aptamer to the surface in order to bring the aptamers to surface height. In some embodiments, the adapter is a nucleic acid adapter (e.g., a sequence of at least about 10, 15, 20, 25, 30, 35, 40, 45, 50, 55, 60, 65, 70, 75, 80, 85, 90, 95 or 100 bases in length). In some embodiments, a sequence complementary to the adapter sequence is hybridized to the adapter prior to aptamer screening. In some embodiments, the adapter is a chemical adapter (e.g., a polymer connecting the aptamer to the surface).

Aptamer Library Screening

In certain aspects, provided herein are methods for identifying one or more aptamers that specifically bind to and/or modulate a target, the method generally comprising: (i) contacting a plurality of aptamer clusters immobilized on a surface with the target; and (ii) identifying the immobilized aptamer clusters that specifically bind to and/or modulate the target. Because the sequence of each aptamer cluster is associated with a specific position on the surface (e.g., determined according to the methods provided herein), the sequence of the aptamer responsible for the binding/modulation is identified and the position at which the target is bound and/or modulated can be determined.

In some embodiments, the target is labeled with and/or comprises a detectable label. The target can be detectably labeled directly (e.g., through a direct chemical linker) or indirectly (e.g., using a detectably labeled target-specific antibody). In embodiments in which the target is a cell, it can be labeled by incubating the target cell with the detectable label under conditions such that the detectable label is internalized by the cell. In some embodiments, the target is detectably labeled before performing the aptamer screening methods described herein. In some embodiments, the target is labeled during the performance of the aptamer screening methods provided herein. In some embodiments, the target is labeled after is it is bound to an aptamer cluster (e.g., by contacting the bound target with a detectably labeled antibody). In some embodiments, any detectable label can be used. Examples of detectable labels include, but are not limited to, fluorescent moieties, radioactive moieties, paramagnetic moieties, luminescent moieties and/or colorimetric moieties. In some embodiments, the targets described herein are linked to, comprise and/or are bound by a fluorescent moiety. Examples of fluorescent moieties include, but are not limited to, Allophycocyanin, Fluorescein, Phycoerythrin, Peridinin-chlorophyll protein complex, Alexa Fluor 350, Alexa Fluor 405, Alexa Fluor 430, Alexa Fluor 488, Alexa Fluor 514, Alexa Fluor 532, Alexa Fluor 546, Alexa Fluor 555, Alexa Fluor 568, Alexa Fluor 594, Alexa Fluor 633, Alexa Fluor 635, Alexa Fluor 647, Alexa Fluor 660, Alexa Fluor 680, Alexa Fluor 700, Alexa Fluor 750, Alexa Fluor 790, EGFP, mPlum, mCherry, mOrange, mKO, EYFP, mCitrine, Venus, YPet, Emerald, Cerulean and CyPet.

The target can be a non-molecular or a supramolecular target. Non-limiting examples of targets to which the aptamers of the present disclosure can bind to and/or modulate include, but are not limited to, cells, bacteria, fungi, archaea, protozoa, viruses, virion particles, synthetic and naturally-occurring microscopic particles, and liposomes. In some embodiments, the target introduced into the flow cell is live/native. In other embodiments, the target introduced into the flow cell is fixed in any solution.

In some embodiments, the target is a cell. In some embodiments, the cell is a prokaryotic cell. In some embodiments, the cell is a bacterial cell. non-limiting examples of bacteria include *Aspergillus, Brugia, Candida, Chlamydia, Coccidia, Cryptococcus, Dirofilaria, Gonococcus, Histoplasma, Klebsiella, Legionella, Leishmania, Meningococci, Mycobacterium, Mycoplasma, Paramecium, Pertussis, Plasmodium, Pneumococcus, Pneumocystis, Pseudomonas, Rickettsia, Salmonella, Shigella, Staphylococcus, Streptococcus, Toxoplasma* and *Vibriocholerae*. Exemplary species include *Neisseria gonorrhea, Mycobacterium tuberculosis, Candida albicans, Candida tropicalis, Trichomonas vaginalis, Haemophilus vaginalis*, Group B *Streptococcus* sp., *Microplasma hominis, Hemophilus ducreyi, Granuloma inguinale, Lymphopathia venereum, Treponema pallidum, Brucella abortus. Brucella melitensis, Brucella suis, Brucella canis, Campylobacter fetus, Campylobacter fetus intestinalis, Leptospira pomona, Listeria monocytogenes, Brucella ovis, Chlamydia psittaci, Trichomonas foetus, Toxoplasma gondii, Escherichia coli, Actinobacillus equuli, Salmonella abortus ovis, Salmonella abortus equi, Pseudomonas aeruginosa, Corynebacterium equi, Corynebacterium pyogenes, Actinobaccilus seminis, Mycoplasma bovigenitalium, Aspergillus fumigatus, Absidia ramosa, Trypanosoma equiperdum, Babesia caballi, Clostridium tetani,* and *Clostridium botulinum*. In some embodiments, the cell is a eukaryotic cell. In some embodiments, the cell is an animal cell (e.g., a mammalian cell). In some embodiments, the cell is a human cell. In some embodiments, the cell is from a non-human animal, such as a mouse, rat, rabbit, pig, bovine (e.g., cow, bull, buffalo), deer, sheep, goat, llama, chicken, cat, dog, ferret, or primate (e.g., marmoset, rhesus monkey). In some embodiments, the cell is a parasite cell (e.g., a malaria cell, a leishmanias cell, a *cryptosporidium* cell or an amoeba cell). In some embodiments, the cell is a fungal cell, such as, e.g., *Paracoccidioides brasiliensis*.

In some embodiments, the cell is a cancer cell (e.g., a human cancer cell). In some embodiments, the cell is from any cancerous or pre-cancerous tumor. Non-limiting examples of cancer cells include cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant, carcinoma, carcinoma, undifferentiated, giant and spindle cell carcinoma, small cell carcinoma, papillary carcinoma, squamous cell carcinoma, lymphoepithelial carcinoma, basal cell carcinoma, pilomatrix carcinoma, transitional cell carcinoma, papillary transitional cell carcinoma, adenocarcinoma, gastrinoma, malignant, cholangiocarcinoma, hepatocellular carcinoma, combined hepatocellular carcinoma and cholangiocarcinoma, trabecular adenocarcinoma, adenoid cystic carcinoma, adenocarcinoma in adenomatous polyp, adenocarcinoma, familial polyposis coli, solid carcinoma, carcinoid tumor, malignant, branchiolo-alveolar adenocarcinoma, papillary adenocarcinoma, chromophobe carcinoma, acidophil carcinoma, oxyphilic adenocarcinoma, basophil carcinoma, clear cell adenocarcinoma, granular cell carcinoma, follicular adenocarcinoma, papillary and follicular adenocarcinoma, nonencapsulating sclerosing carcinoma, adrenal cortical carcinoma, endometroid carcinoma, skin appendage carcinoma, apocrine adenocarcinoma, sebaceous adenocarcinoma, ceruminous adenocarcinoma, mucoepidermoid carcinoma, cystadenocarcinoma, papillary cystadenocarcinoma, papillary serous cystadenocarcinoma, mucinous cystadenocarcinoma, mucinous adenocarcinoma, signet ring cell carcinoma, infiltrating duct carcinoma, medullary carcinoma, lobular carcinoma, inflammatory carcinoma, paget's disease, mammary, acinar cell carcinoma, adenosquamous carcinoma, adenocarcinoma w/squamous metaplasia, thymoma, malignant, ovarian stromal tumor, malignant, thecoma, malignant, granulosa cell tumor, malignant, and roblastoma, malignant, sertoli cell carcinoma, leydig cell tumor, malignant, lipid cell tumor, malignant, paraganglioma, malignant, extra-mammary paraganglioma, malignant, pheochromocytoma, glomangiosarcoma, malignant melanoma, amelanotic melanoma, superficial spreading melanoma, malig melanoma in giant pigmented nevus, epithelioid cell melanoma, blue nevus, malignant, sarcoma, fibrosarcoma, fibrous histiocytoma, malignant, myxosarcoma, liposarcoma, leiomyosarcoma, rhabdomyosarcoma, embryonal rhabdomyosarcoma, alveolar rhabdomyosarcoma, stromal sarcoma, mixed tumor, malignant, mullerian mixed tumor, nephroblastoma, hepatoblastoma, carcinosarcoma, mesenchymoma, malignant, brenner tumor, malignant, phyllodes tumor, malignant, synovial sarcoma, mesothelioma, malignant, dysgerminoma, embryonal carcinoma, teratoma, malignant, struma ovarii, malignant, choriocarcinoma, mesonephroma, malignant, hemangiosarcoma, hemangioendothelioma, malignant, kaposi's sarcoma, hemangiopericytoma, malignant, lymphangiosarcoma, osteosarcoma, juxtacortical osteosarcoma, chondrosarcoma, chondroblastoma, malignant, mesenchymal chondrosarcoma, giant cell tumor of bone, ewing's sarcoma, odontogenic tumor, malignant, ameloblastic odontosarcoma, ameloblastoma, malignant, ameloblastic fibrosarcoma, pinealoma, malignant, chordoma, glioma, malignant, ependymoma, astrocytoma, protoplasmic astrocytoma, fibrillary astrocytoma, astroblastoma, glioblastoma, oligodendroglioma, oligodendroblastoma, primitive neuroectodermal, cerebellar sarcoma, ganglioneuroblastoma, neuroblastoma, retinoblastoma, olfactory neurogenic tumor, meningioma, malignant, neurofibrosarcoma, neurilemmoma, malignant, granular cell tumor, malignant, malignant lymphoma, Hodgkin's disease, Hodgkin's lymphoma, paragranuloma, malignant lymphoma, small lymphocytic, malignant lymphoma, large cell, diffuse, malignant lymphoma, follicular, mycosis fungoides, other specified non-Hodgkin's lymphomas, malignant histiocytosis, multiple myeloma, mast cell sarcoma, immunoproliferative small intestinal disease, leukemia, lymphoid leukemia, plasma cell leukemia, erythroleukemia, lymphosarcoma cell leukemia, myeloid leukemia, basophilic leukemia, eosinophilic leukemia, monocytic leukemia, mast cell leukemia, megakaryoblastic leukemia, myeloid sarcoma, and hairy cell leukemia.

In some embodiments, the target is a virus. For example, in some embodiments, the virus is HIV, hepatitis A, hepatitis B, hepatitis C, herpes virus (e.g., HSV-1, HSV-2, CMV, HAV-6, VZV, Epstein Barr virus), adenovirus, influenza virus, flavivirus, echovirus, rhinovirus, coxsackie virus, coronavirus, respiratory syncytial virus, mumps virus, rotavirus, measles virus, rubella virus, parvovirus, vaccinia virus, HTLV, dengue virus, papillomavirus, molluscum virus, poliovirus, rabies virus, JC virus, or ebola virus In some embodiments, the target is a protein. In certain embodiments, when protein targets are screened they are immobilized on a bead (e.g., a detectably labeled bead). In some embodiments, protein targets are linked to a detectable moiety. Non-limiting examples of target proteins include glycoprotein IIb/IIIa, TNF-α, TNFα receptor, CD52, IL-2Rα, B cell activating factor, VEGF, CD30, IL-1β, epidermal growth factor receptor, CD38, RANK ligand, Complement protein C5, CD11a, CD20, CTLA4, PD-1, PD-L1, PD-L2, CD3, alpha-4 integrin, IgE, RSV F protein, IL-6R, ErbB2, IL-12, and IL-23. In some embodiments, the target protein is a cancer-associated antigen. Examples of cancer-associated antigens include, but are not limited to, adipophilin, AIM-2, ALDH1A1, alpha-actinin-4, alpha-fetoprotein ("AFP"), ALK, ANKRD30A, ARTC1, B-RAF, BAGE-1, BCLX (L), BCR-ABL fusion protein b3a2, beta-catenin, BING-4, BIRC7, CA-125, CA9, CALCA, carcinoembryonic antigen ("CEA"), CALR, CASP-5, CASP-8, CCRS, CD19, CD20, CD22, CD27, CD274, CD30, CD33, CD38, CD40, CD44, CD45, CD52, CD56, CD79, Cdc27, CDK12, CDK4, CDKN2A, CEA, CLEC12A, CLPP, COA-1, CPSF, CSNK1A1, CTAG1, CTAG2, cyclin D1, Cyclin-AL dek-can fusion protein, DKK1, EFTUD2, EGFR, EGFR variant III, Elongation factor 2, ENAH (hMena), Ep-CAM, EpCAM, EphA2, EphA3, epithelial tumor antigen ("ETA"), ERBB3, ERBB4, ETV6-AML1 fusion protein, EZH2, FCRL3, FGFS, FLT3-ITD, FN1, FOLR1, G250/MN/CAIX, GAGE-1,2,8, GAGE-3,4,5,6,7, GAS7, glypican-3, GnTV, gp100/Pme117, GPNMB, GM3, GPR112, IL3RA, HAUS3, Hepsin, HER-2/neu, HERV-K-MEL, HLA-A11, HLA-A2, HLA-DOB, hsp70-2, IDO1, IGF2B3, IL13Ralpha2, Intestinal carboxyl esterase, K-ras, Kallikrein 4, KIF20A, KIT, KK-LC-1, KKLC1, KM-HN-1, KMHN1 also known as CCDC110, KRAS, LAGE-1, LDLR-fucosyltransferaseAS fusion protein, Lengsin, LGRS, LMP2, M-CSF, MAGE-A1, MAGE-A10, MAGE-A12, MAGE-A2, MAGE-A3, MAGE-A4, MAGE-A6, MAGE-A9, MAGE-C1, MAGE-C2, malic enzyme, mammaglobin-A, MART2, MATN, MC1R, MCSP, mdm-2, MEL Melan-A/MART-1, Meloe, Midkine, MMP-2, MMP-7, MUC1, MUC2, MUC3, MUC4, MUC5, MUC5AC, MUC16, mucin, MUM-1, MUM-2, MUM-3, Myosin, Myosin class I, N-raw, NA88-A, neo-PAP, NFYC, NY-BR-1, NY-ESO-1/LAGE-2, OA1, OGT, OS-9, OX40, P polypeptide, p53, PAP, PAX3, PAXS, PBF, PLAC1, PMEL, pml-RARalpha fusion protein, polymorphic epithelial mucin ("PEM"), PPP1R3B, PRAME, PRDXS, PRLR, PSA, PSMA, PTPRK, RAB38/NY-MEL-1, RAGE-1, RBAF600, RET, RGSS, RhoC, RNF43, ROR1, RU2AS, SAGE, SART1, SART3, secernin 1, SIRT2, SLAMF7, SLC39A6, SNRPD1, SOX10, Sp17, SPA17, SSX-2, SSX-4, STEAP1, STEAP2, survivin, SYT-SSX1 or -SSX2 fusion protein, TAG-1, TAG-2, Telomerase, TERT, TGF-betaRII, Thompson-nouvelle antigen, TMPRSS2, TNFRSF17, TPBG, TRAG-3, Triosephosphate isomerase, TRP-1/gp75, TRP-2, TRP2-INT2, tyrosinase, tyrosinase ("TYR"), UPK3A, VEGF, VTCN1, WT1, and XAGE-1b/GAGED2a. In some embodiments, the target protein is a neo-antigen.

In some embodiments, the property of the cell that is modulated is cell viability, cell proliferation, gene expression, cellular morphology, cellular activation, phosphorylation, calcium mobilization, degranulation, cellular migration, and/or cellular differentiation. In certain embodiments, the target is linked to, bound by or comprises a detectable label that allows for the detection of a biological or chemical effect on the target. In some embodiments, the detectable label is a fluorescent dye. Non-limiting examples of fluorescent dyes include, but are not limited to, a calcium sensitive dye, a cell tracer dye, a lipophilic dye, a cell proliferation dye, a cell cycle dye, a metabolite sensitive dye, a pH sensitive dye, a membrane potential sensitive dye, a mitochondrial membrane potential sensitive dye, and a redox potential dye. In one embodiment, the target is labeled with a calcium sensitive dye, a cell tracer dye, a lipophilic dye, a cell proliferation dye, a cell cycle dye, a metabolite sensitive dye, a pH sensitive dye, a membrane potential sensitive dye, a mitochondrial membrane potential sensitive dye, or a redox potential dye.

In certain embodiments, the target is labeled with an activation associated marker, an oxidative stress reporter, an angiogenesis marker, an apoptosis marker, an autophagy marker, a cell viability marker, or a marker for ion concentrations. In yet another embodiment, the target is labeled with an activation associated marker, an oxidative stress reporter, an angiogenesis marker, an apoptosis marker, an autophagy marker, a cell viability marker, or a marker for ion concentrations prior to exposure of aptamers to the target.

In some embodiments, the target is labeled after to exposure of aptamers to the target. In one embodiment, the target is labeled with fluorescently-labeled antibodies, annexin V, antibody fragments and artificial antibody-based constructs, fusion proteins, sugars, or lectins. In another embodiment, the target is labeled with fluorescently-labeled antibodies, annexin V, antibody fragments and artificial antibody-based constructs, fusion proteins, sugars, or lectins after exposure of aptamers to the target.

In some embodiments, the target cell is labeled with a fluorescent dye. Non-limiting examples of fluorescent dyes include, but are not limited to, a calcium sensitive dye, a cell tracer dye, a lipophilic dye, a cell proliferation dye, a cell cycle dye, a metabolite sensitive dye, a pH sensitive dye, a membrane potential sensitive dye, a mitochondrial membrane potential sensitive dye, and a redox potential dye.

In some embodiments, the target cell is labeled with a calcium sensitive dye, a cell tracer dye, a lipophilic dye, a cell proliferation dye, a cell cycle dye, a metabolite sensitive dye, a pH sensitive dye, a membrane potential sensitive dye, a mitochondrial membrane potential sensitive dye, or a redox potential dye. In certain embodiments, the target cell is labeled with an activation associated marker, an oxidative stress reporter, an angiogenesis marker, an apoptosis marker, an autophagy marker, a cell viability marker, or a marker for ion concentrations. In yet another embodiment, target cell is labeled with an activation associated marker, an oxidative stress reporter, an angiogenesis marker, an apoptosis marker, an autophagy marker, a cell viability marker, or a marker for ion concentrations prior to exposure of aptamers to the cell. In some embodiments, the target cell is labeled after to exposure of aptamers to the target. In one embodiment, the target cell is labeled with a fluorescently-labeled antibody or antigen-binding fragment thereof, annexin V, a fluorescently-labeled fusion protein, a fluorescently-labeled sugar, or fluorescently labeled lectin. In one embodiment, the target cell is labeled with a fluorescently-labeled antibody or antigen-binding fragment thereof, annexin V, a fluorescently-labeled fusion protein, a fluorescently-labeled sugar, or fluorescently labeled lectin after exposure of aptamers to the cell.

The position of the detectable marker on the surface can be determined using any method known in the art, including, for example, fluorescent microscopy.

FIG. 1 provides an exemplary workflow illustrating certain embodiments of the methods provided herein. The workflow begins with an initial aptamer library (e.g., an aptamer library provided herein) chosen and prepared as though for Illumina sequencing. The library can be, for example, newly synthesized, or an output of a previous selection process. This process can involve one or more positive selection cycles, one or more negative selection cycles, or both, in either combination and sequence.

The prepared library is mounted on adapters on an Illumina flow cell. Bridge PCR amplification turns each single sequence from the initial library into a cluster of about 100,000 copies of the same sequence. The library is then Illumina-sequenced. This process produces a map linking each sequence from the library to a specific set of coordinates on the flow cell surface.

The complementary strands to those from the library, added in the process of sequencing by synthesis, are stripped by any one of a number of methods (e.g., detergents, denaturing agents, etc.). The oligonucleotide strands complementary to the Illumina adapter and to the PCR primers are then pumped into the flow cell, leaving only the aptamer region single-stranded. When RNA aptamers are being synthesized as part of the library, transcription is initiated and halted by any one of a number of methods (e.g., Ter-bound Tus protein, or biotin-bound streptavidin protein).

The flow cell temperature is raised and then cooled, in order to allow all oligonucleotides on the surface to assume their proper 3D structure, folding according to a folding protocol. In this state, the oligo library is folded and ready to engage targets.

The solution comprising the targets is run into the flow cell using the instrument's hardware. The targets can be labeled prior to introduction into the flow cell/instrument with a fluorescent dye, for the purpose of reporting a biological or chemical effect on the target. The targets are incubated for a certain amount of time to allow the effect to take place. Fluorescent dyes or markers for reporting the biological or chemical effect (e.g., cell activation, apoptosis, etc.) can then be pumped into the flow cell. (See FIG. 1)

Affected targets (hits) are recognized by image analysis, and corresponding sequences are analyzed. Extracted sequences are synthesized and tested separately for binding and function.

EXAMPLES

Example 1—Preparation of Aptamer Library

Aptamer libraries were prepared using an Illumina high throughput sequencing platform sample preparation kits which included the attachment of an adapter DNA sequence on the flanks of the sample sequence to complement strands already attached to the surface of the flow cell. The prepared library was mounted onto adapters on the surface of an Illumina flow cell.

For the preparation of the aptamer libraries, a two-step "tail" PCR process was used to attach the adapters. The PCR reaction mix contained the following components shown in Table 1:

TABLE 1

| Component | Amount in μl |
|---|---|
| Herculase II fusion DNA polymerase | 0.5 |
| buffer | 10 |
| Dntp (10 mM each) | 1.25 |
| Forward tail primer | 1 |
| Reverse tail primer | 1 |
| upw | 35.25 |
| sample | 1 |

The primers were set in a way that adapters would have a specific orientation with respect to the sample sequence. This was done to hold the forward aptamer sequence in the clusters in a single read run.

The sequence of the primers used in 1st PCR reaction:

TruSeq p7 side stab forward primer

[SEQ ID NO: 1]
GTCACATCTCGTATGCCG TCTTCTGCTTG ATCCAGAGTGACGCAGCA;
and

TruSeq p5 side stab reverse primer

[SEQ ID NO: 2]
CTCTTTCCCTACACGACG CTCTTCCGATCT ACTAAGCCACCGTGTCCA

The PCR program used for the first reaction is shown herein below in Table 2:

TABLE 2

| Step | Temperature | Time (seconds) |
|---|---|---|
| 1 | 95 | 180 |
| 2 | 95 | 30 |
| 3 | 56 | 10 |
| 4 | 72 | 10 |
| 5 | Return to step 2 × 3 | |
| 6 | 95 | 30 |
| 7 | 85 | 10 |
| 8 | 72 | 10 |
| 9 | Return to step 6 × 10 | |
| 10 | 4 | Forever |

The product of first PCR reaction (PCR 1) is the input for the 2nd PCR reaction.

The sequence of the primers used in the 2nd PCR reaction:

TruSeq p7 side start

[SEQ ID NO: 3]
GATCGGAAGAGCACACGTCTGAACTCCAGTCACATCTCGTATGCCG;
and

TruSeq p5 side start

[SEQ ID NO: 4]
AATGATACGGCGACCACCGAGATCTACACACACTCTTTCCCTACACGACG.

The PCR program used for the second reaction is shown herein below in Table 3:

TABLE 3

| Step | Temperature | time |
|---|---|---|
| 1 | 95 | 30 |
| 2 | 67 | 10 |
| 3 | 72 | 10 |
| 4 | 95 | 30 |
| 5 | 65 | 10 |
| 6 | 72 | 10 |
| 7 | 95 | 30 |
| 8 | 63 | 10 |

TABLE 3-continued

| Step | Temperature | time |
|---|---|---|
| 9 | 72 | 10 |
| 10 | 95 | 30 |
| 11 | 62 | 10 |
| 12 | 72 | 10 |
| 13 | 95 | 30 |
| 14 | 87 | 10 |
| 15 | 72 | 10 |
| 16 | Return to step 13 × 1 | |
| 17 | 95 | 30 |
| 18 | 85 | 10 |
| 19 | 72 | 10 |
| 20 | Return to step 17 × 7 | |
| 21 | 4 | Forever |

Completed libraries underwent quality control which included qbit check for concentration and tapstation/fragment analyzer to check for library size and byproducts. Cluster generation and sequencing was carried out according to the sequencing platform and Illumina protocols. After the sequencing process, denaturation provides the clusters in a single strand form. Adapters and primers are then blocked and aptamers will fold to their 3d conformation in their folding buffer.

Generation and Sequencing of Clusters

Bridge PCR amplification was used to turn each single sequence from the initial library into a cluster of about 100,000 copies of the same sequence. The cluster library was then Illumina-sequenced. This process produced a map linking each sequence from the library to a specific set of coordinates on the flow cell surface.

The complementary strands to those from the library, added in the process of sequencing by synthesis, were stripped and oligonucleotide strands complementary to the Illumina adapter and to the PCR primers were pumped to the flow cell, leaving only the aptamer region single-stranded. In case of RNA aptamers, transcription was initiated and halted by any one of a number of methods (e.g., Ter-bound Tus protein, or biotin-bound streptavidin protein).

The flow cell temperature was raised and then cooled, to allow all oligonucleotides on the surface of the flow cell to assume their proper 3D conformation in the appropriate folding buffer. For example, one folding buffer recipe used (cellselex paper) included 1 liter PBS, 5 ml of 1M $MgCl_2$, and 4.5 g glucose Target Introduction Target (e.g., cells, bacteria, particles, viruses, proteins, etc.) were introduced into the system in the desired binding buffer according to the environment they would be used in (e.g., human serum, PBS, 1b) using the machine's hardware. One option for a general binding buffer recipe is (cellselsex paper): 1 liter PBS, 5 ml 1M $MgCl_2$, 4.5 g glucose, 100 mg tRNA, and 1 g BSA. Targets were labeled prior to or after introduction into the flow cell/machine and incubated for a certain amount of time to let effect take place.

Targets can be labeled using different fluorophore that will fit the platforms excitation source and emission filters. Labeling can be done through any possible docking site available on the target. Examples of labeling agents include, but are not limited to, DiI, anti HLA+secondery Dylight 650, anti HLA PE-CyS, and Dylight 650.

For the screening of functional aptamers, fluorescent reporters can be used to visualize the effect. For example, introduction of 7AAD to the flow cell can be used to label the targets to screen for cell death, or annexin V fluorophore conjugate can be used to label the targets to screen for apoptosis. The reporter agent, its concentration, time of incubation and specific recipe protocol should be adjusted in accordance with the specific effect screening for.

Representative Method for Sequencing Initial Library Followed by Target Cell Introduction and Acquisition of Functional Oligonucleotide Clusters 80 µl of "Incorporation Mix Buffer" is pumped into the flow cell at a rate of 250 µl/min. The temperature is then set temperature to 55° C. 60 µl of "Incorporation Mix" is pumped to the flow cell at a rate of 250 µl/min and after 80 seconds 10 µl of "Incorporation Mix" is pumped to the flow cell at a rate of 250 µl/min. After 211 seconds, the temperature is set to 22° C. and 60 µl of "Incorporation Mix Buffer" is pumped to the flow cell at a rate of 250 µl/min. 75 µl of "Scan Mix" is then pumped into to the flow cell at a rate of 250 µl/min.

The method then calibrates to focus to the plane of the clusters and align microscope and flow cell planes. 100 µl of "Incorporation Mix Buffer" is pumped into to the flow cell at a rate of 250 µl/min. The incorporation steps above are repeated 99 times.

The temperature control is turned off and 125 µl of "Cleavage Buffer" is pumped into the flow cell at a rate of 250 µl/min. The temperature is then set to 55° C. and 75 µl of "Cleavage Mix" pumped into the to the flow cell at a rate of 250 µl/min. After 80 seconds, 25 µl of "Cleavage Mix" is pumped into the flow cell at a rate of 250 µl/min After an addition 80 seconds, 25 µl of "Cleavage Mix" is pumped into the flow cell at a rate of 250 µl/min. After 80 seconds, the temperature is set to 22° C. The temperature control is then turned off and 60 µl of "Incorporation Mix Buffer" is pumped into the flow cell at a rate of 250 µl/min. The volume remaining in each water tube is then checked to verify proper delivery.

Denaturation then takes place followed by capping. For the denaturation steps, the temperature is then set to 20° C. for 120 seconds. 75 µl of "Wash Buffer" is pumped into the flow cell at a rate of 60 µl/min, followed by 75 µl of "Denaturation Solution" at a rate of 60 µl/min and 75 µl of "Wash Buffer" at a rate of 60 µl/min.

For the capping steps, 75 µl of "Wash Buffer" is pumped into the flow cell at a rate of 60 µl/min and the temperature is set to 85° C. for 120 seconds. 80 µl of "5' Cap" is then pumped into the flow cell at a rate of 80 µl/min and the temperature is set to 85° C. for 30 seconds. 10 µl of "5' Cap" is pumped into the flow cell at a rate of 13 µl/min and the temperature is set to 85° C. for 60 seconds. 10 µl of "5' Cap" is pumped into the flow cell at a rate of 13 µl/min and the temperature is set to 85° C. for 90 seconds. 10 µl of "5' Cap" is pumped into to the flow cell at a rate of 13 µl/min and the temperature is set to 85° C. for 120 seconds. 10 µl of "5' Cap" is pumped into the flow cell at a rate of 13 µl/min and the temperature is set to 85° C. for 150 seconds.

10 µl of "5' Cap" is pumped into the flow cell at a rate of 13 µl/min and the temperature is set to 85° C. for 180 seconds. 10 µl of "5' Cap" is pumped into the flow cell at a rate of 13 µl/min and the temperature is set to 85° C. for 210 seconds. 10 µl of "5' Cap" is pumped into the flow cell at a rate of 13 µl/min and the temperature is set to 85° C. for 240 seconds. 10 µl of "5' Cap" is pumped into the flow cell at a rate of 13 µl/min and the temperature is set to 85° C. for 270 seconds. 75 µl of "Wash Buffer" is pumped into the flow cell at a rate of 60 µl/min and the temperature is set to 85° C. for 120 seconds.

For the 3' Cap, 80 µl of "3' Cap" is pumped into the flow cell at a rate of 80 µl/min and the temperature is set to 85° C. for 30 seconds. 10 µl of "3' Cap" is pumped into the flow cell at a rate of 13 μl/min and the temperature is set to 85° C. for 60 seconds. 10 μl of "3' Cap" is pumped into the flow cell at a rate of 13 μl/min and the temperature is set to 85° C. for 90 seconds. 10 μl of "3' Cap" is pumped into the flow cell at a rate of 13 μl/min and the temperature is set to 85° C. for 120 seconds. 10 μl of "3' Cap" is pumped into the flow cell at a rate of 13 μl/min and the temperature is set to 85° C. for 150 seconds. 10 μl of "3' Cap" is pumped into the flow cell at a rate of 13 μl/min and the temperature is set to 85° C. for 180 seconds. 10 μl of "3' Cap" is pumped into the flow cell at a rate of 13 μl/min and the temperature is set to 85° C. for 210 seconds. 10 μl of "3' Cap" is pumped into the flow cell at a rate of 13 μl/min and the temperature is set to 85° C. for 240 seconds.

10 μl of "3' Cap" is pumped into the flow cell at a rate of 13 μl/min and the temperature is set to 85° C. for 270 seconds. 75 μl of "Wash Buffer" is pumped into the flow cell at a rate of 60 μl/min and the temperature is set to 0° C. 200 μl of "Folding Buffer (chilled)" is pumped into the flow cell at a rate of 250 μl/min followed by 160 μl of "Folding Buffer (chilled)" at a rate of 40 μl/min and the temperature is set to 0° C. for 600 seconds.

The temperature is raised to 37° C. for 120 seconds. This is followed by a binding step.

For the binding step, 80 μl of "Binding Buffer" is pumped into the flow cell at a rate of 250 μl/min and the temperature is set to 37° C. 80 μl of "Target #1" is pumped into the flow cell at a rate of 100 μl/min and the temperature is set to 37° C. for 300 seconds. 10 μl of "Target #1" is again pumped into the flow cell at a rate of 13 μl/min and the temperature is set to 37° C. for 300 seconds. Lastly, 10 μl of "Target #1" is pumped into to the flow cell at a rate of 13 μl/min and the temperature is set to 37° C. for 2700 seconds.

This is followed by a three consecutive incorporation stepsn and wash steps to remove unbound target consisting of incorporation, pumping 80 μl of "Binding Buffer" into the flow cell at a rate of 13 μl/min, incorporation, pumping 80 μl of "Binding Buffer" into the flow cell at a rate of 80 μl/min, incorporation, pumping 80 μl of "Binding Buffer" into the flow cell at a rate of 200 μl/min and incorporation.

The denaturing, capping, binding, incorporation and washing steps above are repeated until sequencing and target introduction is complete. Various targets are then added and binding to and/or activity of the aptamers is evaluated.

Figure 3:
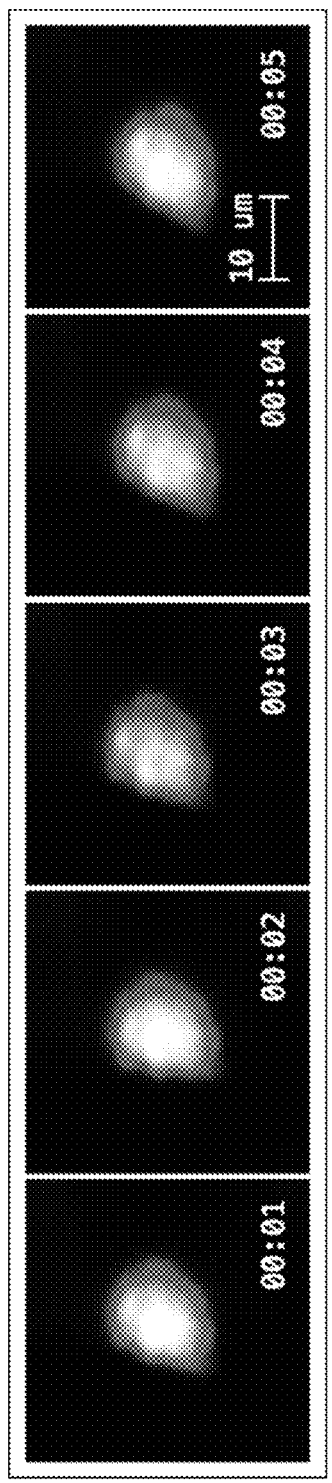
FIG. 3 is an image of a cell bound to aptamers on a flow cell. The image shows the movement of the cell relative to the surface over time. The image shows that the cell is retained by the immobilized aptamer cluster, rather than attached to the surface itself, and is thus free to move but confined to that location. Imaging was performed on an Illumina GAIIx.

FIG. 3 shows a time lapse image of the movement of a Hana cell bound to the flow cell. The results demonstrate that the cell is actually bound by the sequences attached to the surface itself, rather than the surface itself, and is thus free to move but confined to that location.

Example 2—Functional Aptamer Identification

An embodiment of the method provided herein was used to identify aptamers that induce apoptosis in freshly isolated (12 hr) human triple negative breast cancer cells.

An aptamer library as described herein was immobilized on a flow cell and bridge PCR was performed in an Illumina instrument to generate a clustered library. During the amplification process the clustered library was sequenced according to the Illumina protocol with the exception that PBS was used in place of bleaching reagent at the end of the sequencing process so that the flow cell was not destroyed following sequencing. The known probes made up 0.1-1% of the library so that the resulting sequencing map could be aligned to later generated fluorescent microscope images.

After the final PBS wash, the flow cell was loaded onto a fluorescent microscope with temperature control, and clusters were imaged at phase to view clusters and in the green fluorescence channel to view the apoptosis indicator. The coordinates of the known probe sequences were used to align the microscope-generated image with the sequence cluster map generated during the sequencing process by the sequencer.

Freshly isolated human breast cancer cells from bone marrow aspirate were prepared at $10^6$ cells/mL concentration to achieve an average cell density of ~1 per 100 micron$^2$ on the flow cell chamber floor in PBS containing 1% albumin and 1 mM $Mg^{2+}$. Target cells were loaded with a green fluorescent caspase 3/7 activity reporter dye as per the manufacturer's instructions and washed. Cells were pumped into the flow cell using a syringe pump.

The flow cell was imaged at t=0 in Phase and Green channel and then incubated at 37 degrees and imaged again at 30 minute intervals. Aptamer-induced apoptosis was detected by green fluorescence when the target cell was engaged by a functional aptamer. Cells were washed with the same buffer under increasing pump pressure and further imaged to identify functional aptamers that had a higher affinity for the target cells.

The clustered aptamer library analysis was repeated using peripheral blood mononuclear cells as a counter-target in a different lane of the flow-cell using the same sequenced library to identify target-specific aptamer sequences. Computational analysis was performed to translate coordinates at which target or counter-target cells bound to aptamer clusters and underwent apoptosis to identify aptamer sequences that preferentially mediated apoptotic function in the target cells versus the counter-target cells. More than 1,000 aptamers capable of specifically mediating target-selective apoptosis on tumor cells from the specific donor were successfully identified from the library.

Example 3—Functional Aptamer Identification in an Illumina Sequencer

An embodiment of the method provided herein is used to identify aptamers that induce apoptosis in freshly isolated (12 hr) human tumor cells.

An aptamer library as described herein is immobilized on a flow cell and bridge PCR was performed in an Illumina instrument to generate a clustered library. During the amplification process the clustered library is sequenced according to the Illumina protocol with the exception that PBS was used in place of bleaching reagent at the end of the sequencing process so that the flow cell is not destroyed following sequencing.

After the final PBS wash, the clusters are imaged in the Illumina Instrument in the green fluorescence channel to view the apoptosis indicator. Freshly isolated human breast cancer cells from bone marrow aspirate are prepared at $10^6$ cells/mL concentration to achieve an average cell density of ~1 per 100 micron$^2$ on the flow cell chamber floor in PBS containing 1% albumin and 1 mM $Mg^{2+}$. Target cells are loaded with a green fluorescent caspase 3/7 activity reporter dye as per the manufacturer's instructions and washed. Cells are pumped into the flow cell using the Illumina instrument.

An additional sequencing cycle is run during which the flow cell is imaged. The position of target cells within the flow cell is determined based on the presence of a cell-specific fluorescent signal. Aptamer-induced apoptosis is detected by the appearance of fluorescent signal at flow cell coordinates associated with one or more aptamer clusters. Cells appear to the sequencer as "spots" of several clusters.

Target cells undergoing apoptosis are identified based the fluorescence emission of the activity reporter dye.

The clustered aptamer library analysis is repeated using non-tumor cells as a counter-target in a different lane of the flow-cell using the same sequenced library to identify target-specific aptamer sequences. Computational analysis is performed to translate coordinates at which target or counter-target cells bound to aptamer clusters and underwent apoptosis to identify aptamer sequences that preferentially mediated apoptotic function in the target cells versus the counter-target cells. Aptamers capable of specifically mediating target-selective apoptosis on tumor cells from the specific donor are identified from the library.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method for identifying one or more aptamers that interact with a target cell, the method comprising:
   (i) contacting a plurality of aptamer clusters immobilized on a surface with a target cell wherein at least $10^2$ distinct aptamer clusters are immobilized on the surface, and wherein each aptamer cluster:
      (1) is of a known sequence; and
      (2) is at a known position on the surface;
   (ii) determining positions on the surface at which the target cell is retained; and
   (iii) identifying the aptamer clusters immobilized on the surface at the positions at which the target cell is retained as the immobilized aptamer clusters that interact with the target cell.

2. The method of claim 1, wherein the surface is a surface of a flow cell.

3. The method of claim 1, further comprising the steps of:
   (a) immobilizing a plurality of aptamers from an aptamer library on a surface; and
   (b) amplifying the plurality of immobilized aptamers locally on the surface to form the plurality of immobilized aptamer clusters.

4. The method of claim 3, wherein the amplification is conducted via bridge PCR amplification or rolling circle amplification.

5. The method of claim 4, wherein the method further comprises removing the complementary strands from the immobilized aptamer clusters to provide single stranded immobilized aptamer clusters.

6. The method of claim 1, further comprising an aptamer folding step, wherein the aptamer folding step comprises raising and then lowering the temperature of the aptamer clusters.

7. The method of claim 1, further comprising an aptamer folding step, wherein the aptamer folding step comprises adding a denaturing agent to the aptamer clusters and then removing the denaturing agent from the aptamer clusters.

8. The method of claim 1, wherein the immobilized aptamer clusters are sequenced before step (i).

9. The method of claim 8, wherein the sequencing is conducted via Illumina sequencing or Polonator sequencing.

10. The method of claim 1, wherein at least $10^8$ distinct aptamers are immobilized on the surface and each aptamer cluster comprises $10^3$ to $10^6$ copies of an aptamer.

11. The method of claim 1, wherein the target cell is labeled with a reporter of cell function.

12. The method of claim 11, wherein the cell function is apoptosis, caspase-3/7 activity, proliferation, gene expression, or cytokine expression.

13. The method of claim 11, comprising the step of identifying the immobilized aptamer clusters that mediate a cell function in the target cell by detecting the reporter of cell function.

14. The method of claim 13, wherein the cell function is apoptosis.

15. The method of claim 1, wherein the positions on the surface at which the target molecule is retained are determined by fluorescent microscopy.

16. The method of claim 1, wherein the aptamers in the aptamer cluster comprise nucleic acid adapters binding the aptamers to the surface.

17. The method of claim 16, wherein a sequence complementary to the nucleic acid adapter sequence is hybridized to the adapter prior to step (i).

18. A method for identifying one or more aptamers that mediate a functional effect on a target cell, the method comprising:
   (i) contacting a plurality of aptamer clusters immobilized on a surface with a target cell labeled with a reporter of cell function, wherein at least $10^2$ distinct aptamer clusters are immobilized on the surface, and wherein each aptamer cluster:
      (1) is of a known sequence; and
      (2) is at a known position on the surface;
   (ii) determining positions on the surface at which the target cell undergoes the functional effect by detecting the reporter of cell function; and
   (iii) identifying the aptamer clusters immobilized on the surface at the positions at which the target cell undergoes the functional effect as the immobilized aptamer clusters that mediate the functional effect on the target cell.

19. The method of claim 18, wherein the surface is a surface of a flow cell.

20. The method of claim 18, wherein the reporter of cell function is a fluorescent reporter of cell function.

21. The method of claim 18, further comprising the steps of:
   (a) immobilizing a plurality of aptamers from an aptamer library on a surface; and
   (b) amplifying the plurality of immobilized aptamers locally on the surface to form the plurality of immobilized aptamer clusters.

22. The method of claim 21, wherein the amplification is conducted via bridge PCR amplification or rolling circle amplification.

23. The method of claim 18, wherein the immobilized aptamer clusters are sequenced before step (i).

24. The method of claim 18, wherein at least $10^8$ distinct aptamers are immobilized on the surface and each aptamer cluster comprises $10^3$ to $10^6$ copies of an aptamer.

25. The method of claim 20, wherein the positions on the surface at which the target cell undergoes the functional effect are determined by fluorescent microscopy.

26. The method of claim 18, wherein the functional effect is cell death, caspase-3/7 activity, proliferation, gene expression, or cytokine expression.

27. The method of claim 18, wherein the functional effect is cell death and the reporter of cell function is a cell death reporter.

28. The method of claim 27, wherein the cell death reporter is 7-AAD or Annexin V.

29. The method of claim 27, wherein the cell death is apoptosis and the cell death reporter is a fluorescent indicator of apoptosis.

30. The method of claim 29, wherein the fluorescent indicator of apoptosis is Annexin V or green fluorescent caspase 3/7 activity reporter dye.

* * * * *